US006790648B2

(12) United States Patent
Wang et al.

(10) Patent No.: US 6,790,648 B2
(45) Date of Patent: Sep. 14, 2004

(54) DNA FRAGMENTATION FACTOR INVOLVED IN APOPTOSIS

(75) Inventors: Xiaodong Wang, Dallas, TX (US); Xuesong Liu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 161 days.

(21) Appl. No.: 09/748,451

(22) Filed: Dec. 22, 2000

(65) Prior Publication Data

US 2001/0011078 A1 Aug. 2, 2001

Related U.S. Application Data

(62) Division of application No. 09/061,702, filed on Apr. 16, 1998, now Pat. No. 6,165,737.

(51) Int. Cl.[7] ............... C12N 9/22; C12N 15/55; C12N 14/79; C07K 14/435

(52) U.S. Cl. ............... 435/196; 530/300; 530/321; 530/326; 435/69.1; 435/252.3; 435/320.1; 536/23.2

(58) Field of Search ............... 435/196; 530/300, 530/324, 326; 536/23.2

(56) References Cited

U.S. PATENT DOCUMENTS 5,912,141 A 6/1999 Brojatsch et al. .......... 435/69.1

FOREIGN PATENT DOCUMENTS

WO WO 99/10501 A1 * 3/1999

OTHER PUBLICATIONS

Alnemri et al., "Human ICE/CED–3 protease nomenclature," *Cell*, 87:171, 1996.
Casicola–Rosen et al., "Apopain/CPP32 cleaves proteins that are essential for cellular repair: a fundamental principle of apoptotic death," *J. Exp. Med.*, 183:1957–1964, 1996.
Chinnaiyan et al., "Molecular ordering of the cell death pathway," *J. Biol. Chem.*, 271(9):4573–4576, 1996.
Darmon et al., "Cleavage of CPP32 by granzyme B represents a critical role for granzyme B in the induction of target cell DNA fragmentation," *J. Biol. Chem.*, 271:21709–21712, 1996.
Datta et al., "Activation of the CPP32 protease in apoptosis induced by 1–β–D–arabinofuranosylcytosine and other DNA–damaging agents," *Blood*, 88(6):1936–1943, 1996.
Datta et al., "Activation of a CrmA–insensitive, p35–sensitive pathway in ionizing radiation–induced apoptosis," *J. Biol. Chem.*, 272(3):1965–1969, 1997.
Dubrez et al., "Pivotal role of a DEVD–sensitive step in etoposide–induced and Fas–mediated apoptotic pathways," *J. EMBO.*, 15(20):5504–5512, 1996.

(List continued on next page.)

*Primary Examiner*—Nashaat Nashed
*Assistant Examiner*—William W. Moore
(74) *Attorney, Agent, or Firm*—Fulbright & Jaworski L.L.P.

(57) ABSTRACT

The invention provides methods and compositions relating to DNA Fragmentation Factor (DFF) polypeptides and related nucleic acids. More particularly, the present invention provides the sequence for the active subunit of DFF. The polypeptides may be produced recombinantly from host cells transformed from the disclosed DFF encoding nucleic acids or purified from human cells. The invention provides isolated DFF, hybridization probes and primers capable of specifically hybridization with the disclosed DFF genes, DFF-specific binding agents such as specific antibodies, and methods of making and using the subject compositions.

5 Claims, 1 Drawing Sheet

Comparison of Human DFF40 and Mouse CAD

```
  1 MCAVLRQPKCVKLRALHSACKFGVAARSCQELLRKGCVRFQLPMPGSRLCLY  50
    :|..||:|||||:|: |||||:|||||:||||:||||| .||||||
  1 MLQKPKSVKLRALRSPRKFGVAGRSCQEVLRKGCLRFQLPERGSRLCLY    49

51 EDGTEVTDDCFPGLPNDAELLLLTAGETWHGYVSDITRFLSVFNEPHAGV   99
    |||||:|||:|..:|::|||:||| |:.|:||||| ||||.|:||:.|:
 50 EDGTELTEDYFPSVPDNAELVLLTLGQAWQGYVSDIRRFLSAFHEPQVGL  99

100 IQAARQLLSDEQAPLRQKLLADLLHHVSQNITAETREQDPSWFEGLESRF 149
    ||||.|||:||||| ||:|||||||:|||||.||||.:||.|||||||||
100 IQAAQQLLCDEQAPQRQRLLADLLHNVSQNIAAETRAEDPPWFEGLESRF 149

150 RNKSGYLRYSCESRIRGYLREVSAYTSMVDEAAQEEYLRVLGSMCQKLKS 199
    ..|||||||||||||:|||||.|.| |:..||||:||||||||:|:1
150 QSKSGYLRYSCESRIRSYLREVSSYPSTVGAEAQEEFLRVLGSMCQRLRS 199

200 VQYNGSYFDRGAEASSRLCTPEGWFSCQGPFDLESCLSKHSINPYGNRES 249
    :|||||||||.::||||||||||||||||::||||:|||||:||||
200 MQYNGSYFDRGAKGGSRLCTPEGWFSCQGPFDMDSCLSRHSINPYSNRES 249

250 RILFSTWNLDHIIEKKRTVVPTLAEAI..QDGREVNWEYFYSLLFTAENL 297
    |||||||||||||||::|||.||| |||||:|||||:||||.|||
250 RILFSTWNLDHIIEKKRTIIPTLVEAIKEQDGREVDWEYFYGLLFTSENL 299

298 KLVHIACHKKTTHKLECDRSRIYRPQTGSRRKQPARKKRAPARKRD      342
    ||||.||||||||:||.||||:||| :||||.||:.
300 KLVHIVCHKKTTHKLNCDPSRIYKPQTRLKRKQPVRKRQ             338
```

OTHER PUBLICATIONS

Enari et al., "Sequential activation of ICE–like and CPP32–like proteases during Fas–mediated apoptosis," *Nature*, 380:723–726, 1996.Enari et al., "A caspase–activated Dnase that degrades DNA during apoptosis, and its inhibitor ICAD," *Nature*, 391(1):43–50, 1998.

Erhardt and Cooper, "Activation of the CPP32 apoptotic protease by distinct signaling pathways with differential sensitvity to Bcl–$x_L$," *J. Biol. Chem.*, 271(30):17601–17604, 1996.

Faleiro et al., "Multiple species of CP 32 and Mch2 are the major active caspases present in apoptotic cells," *J. EMBO*, 16:2271, 1997.

Fernandes–Alnemri et al., "CPP32, a novel human apoptotic protein with homology to *caenorhabditis elegans* cell death protein Ced–3 and mammalian interleukin–1β–converting enzyme," *J. Biol. Chem.*, 269(49):30761–30764, 1994.

Goldberg et al., "Cleavage of huntingtin by apopain, a proapoptotic cystein protease, is modulated by the polyglutamine tract," *Nat. Genet.*, 13(4):442–449, 1996.

Hartl et al., "Molecular chaperones in protein folding: the art of avoiding sticky situations", *TIBS*, 19:20, 1994.

Hasegawa et al., "Involvement of CPP32/Yama(–like) proteases in Fas–mediated apoptosis," *Cancer Res.*, 56:1713–1718, 1996.

Jackson et al., "Chromatin fractionation procedure that yields nucleosomes containing near–stoichiometric amounts of high mobility group nonhistone chromosomal proteins," *Biochemistry*, 18:3739–3748, 1979.

Jacobson et al., "Role of Ced–3/ICE–family proteases in staurosporine–induced programmed cell death," *J. Cell. Biol.*, 133(5):1041–1051, 1996.

Kaufman et al., "Specific proteolytic cleavage of poly(ADP–ribose) polymerase: an early mark chemotherapy–induced apoptosis," *Cancer Res.*, 53:3976–3985, 1993.

Kerr et al., "Apoptosis: a basic biological phenomenon with wide–ranging implications in Tissue Kinetics," *Br. J. Cancer*, 26:239, 1972.

Khokhlatchev et al., "Reconstitution of mitogen–activated protein kinase phosphorylation cascades in bacteria," *J. Biol. Chem.*, 272(17):11057–11062, 1997.

Kuida et al., "Decreased apoptosis in the brain and premature lethality in CPP320–deficient mice," *Nature*, 384:368–372, 1996.

Lazebnik et al., "Studies of the lamin proteinase reveal multiple parallel biochemical pathways during apoptotic execution," *Proc. Natl. Acad. Sci. USA*, 92:9042–9046, 1995.

Liu et al., "Induction of Apoptotic Program in Cell–Free Extracts: Requirement for dATP and Cytochrome c," *Cell*, 86:147–157, 1996.

Liu et al., "DFF, a heterodimeric protein that functions downstream of Caspase–3 to trigger DNA fragmentation during apoptosis," *Cell*, 89:175–184, 1997.

Liu et al., "Purification and Characterization of an Interleukin–1β–converting Enzyme Family Protease that Activates Cysteine Protease P32 (CPP32)*," *J. Biol. Chem.*, 271:13371–13376, 1996.

Luo and Sawadogo, "Functional domains of the transcription factor USF2: Atypical nuclear localization signals and context–dependent transcriptional activation domains," *Mol. Cell Biol.*, 16(4):1367–1375, 1996.

Martin et al., The cytotoxic cell protease granzyme B initiates apoptosis in a cell–free system by proteolytic processing and activation of the ICE/CED–3 family protease, CPP32, *via* a novel two–step mechanism, *J. EMBO*, 15(10):2407–2416, 1996.

Martins et al., "Activation of multiple interleukin–1β converting enzyme homologues in cytosol and nuclei of HL–60 cells during etoposide–induced apoptosis," *J. Biol. Chem.*, 272:7421–7430, 1997.

Na et al., "D4–GDI, a substrate of CPP32, is proteolyzed during Fas–induced apoptosis," *J. Biol. Chem.*, 271(19):11209–11213, 1996.

Nicholson and Thornberry, "Caspases: killer proteases," *TIBS*, 257:299–306, 1997.

Nicholson et al., "Identification and inhibition of the ICE/CED–3 protease necessary for mammalian apoptosis," *Nature*, 376:37–43, 1995.

Paine et la., "Protein loss during nuclear isolation," *J. Cell Biol.*, 97:1240–1242, 1983.

Peters et al., "Evidence for the location of high mobility group protein T in the internucleosomal linker regions of trout testis chromatin," *J. Biol. Chem.*, 254:3358–3361, 1979.

Rädler et al., "Structure of DNA–cationic liposome complexs DNA intercalation in multilamellar membranes in distinct interhelical packing regimes," *Science*, 275:810–814, 1997.

Roche et al., "The involvement of histone H1o in chromatin structure," *Nucleic Acids Res.*, 13:2843–2853, 1985.

Sakahira et al., "Cleavage of CAD inhibitor in CAD activation and DNA degradation during apoptosis," *Nature*, 391(1):96–99, 1998.

Schlegel et al., "CPP32/Apopain is a key interleukin 1β converting enzyme–like protease involved in Fas–mediated apoptosis," *J. Biol. Chem.*, 271:1841–1844, 1996.

Schroter and Bode, "The binding sites for large and small high–mobility–group (HMG) proteins," *Eur. J. Biochem.*, 127:429–436, 1982.

Shiraishi et al., "Adenovirus–mediated gene transfer using in–situ perfusion of the liver graft," *Transplant International*, 1–0(3):202–206, 1997.

Smith and Moss, "Infectious poxvirus vectors have capacity for at lease 25000 base pairs of foreign DNA," *Gene*, 25:21–28, 1983.

Song et al., "DNA–dependent protein kinase catalytic subunit: a target for an ICE–like protease in apoptosis," *J. EMBO*, 15(3):3238–3246, 1996.

Song et al., "DCP–1, a *drosophila* cell death protease essential for development," *Science*, 275:536–540, 1997.

Sun et al., "Separate metabolic pathways leading to DNA fragmentation and apoptotic chromatin condensation," *J. Exp. Med.*, 179:559–568, 1994.

Takahashi et al., "Affinity labeling displays the stepwise activation of ICE–related proteases by Fas, staurosporine, and CrmA–sensitive caspase–8," *Oncogene*, 14:2741–2752, 1997.

Tam et. la., "$SN^2$ deprotection of synthetic peptides with a low concentration of HF in dimethyl sulfide: evidence and application in peptide synthesis," *J. Am. Chem. Soc.*, 105:6442–6455, 1983.

Tewari et al., "Yama/CPP32β, a mammalian homolog of CED–3, is a CrmA–inhibitable protease that cleaves the death substrate poly(ADP–ribose) polymerase," *Cell*, 81:801–809, 1995.

Vaux, "CED–4—The third horseman of apoptosis," *Cell*, 90:389–390, 1997.

Walther and Stein, "Cell type specific and inducible promoters for vectors in gene therapy as an approach for cell targeting," *J. Mol. Med.*, 74:379–392, 1996.

Wang et al., "Cleavage of sterol regulatory element binding proteins (SREBPs) by CPP 32 during apoptosis," *J. EMBO*, 15:1012–1020, 1996.

Wang et al., "Mice lacking ADPRT and ply(ADP–ribosyl)ation develop normally but are susceptible to skin disease," *Gene & Dev.*, 9:509–520, 1995.

Wang et al., "Nuclear protein that binds sterol regulatory element of low density lipoprotein receptor promoter," *J. Biol. Chem.*. 268(19):14497–14504, 1993.

Wang et al., "Purification of an interleukin–1β converting enzyme–related cystein protease that cleaves sterol regulatory element–binding proteins between the leucine zipper and transmemebrane domains," *J. Biol. Chem.*, 270(30):18044–18050, 1995.

Wang et al., "R–ras promotes apoptosis caused by growth factor deprivation via a Bcl–2 suppressible mechanism," *J. Cell Biol.*, 129:1103–1114, 1995.

White, "Life, death, and the pursuit of apoptosis," *Genes & Dev.*, 10:1–15, 1996.

Wong et al., "Appearance of β–lactamase activity in animal cells upon liposome–mediated gene transfer," *Gene*, 10:87–94, 1980.

Wyllie, "An endonuclease at last," *Nature*, 391:20–21, 1998.

Wyllie et al., "Cell Death: The Significance of Apoptosis," *Int. Rev. Cytol.*, 68:251–306, 1980.

Wyllie et al., "Chromatin cleavage in apoptosis: association with condensed chromatin morphology and dependence on macromolecular synthesis," *J. Pathol.*, 142:67–77, 1984.

Wyllie, "The genetic regulation of apoptosis," *Curr. Opin. in Genet. Dev.*, 5:97–104, 1995.

Xue et al. "The Caenorhabditis elegans cell–death protein CED–3 is a cysteine protease with substrate specificities similar to thos eo the human CPP32 protease," *Genes & Dev.*, 10:1073–1083, 1996.

Yokoyama et al., "SREBP–1, a basic–helixs–loop–helix–leucine zipper protein that controls transcription of the low density lipoprotein receptor gene," *Cell*, 75:187–197, 1993.

Yuan et al., "The C. Elegans Cell Death Gene ced–3 Encodes a Protein Similar to Mammalian Interleukin–1β–Converting Enzyme," *Cell*, 75:641–652, 1993.

Zamzami et al., "Mitochondrial control of nuclear apoptosis," *J. Exp. Med.*, 183:1533–1544, 1996.

Zou et al., "Apaf–1, a Human Protein Homologous to C. elegans CED–4, Participates in Cytochrome c–Dependent Activation of Caspase–3," *Cell*, 90:405, 1997.

Halenbeck et al., "CPAN, a human nuclease regulated by the caspase–sensitive inhibitor DFF45," *Current Biology*, 8:527–540, 1998.

International Search Report dated Jan. 22, 1999 (PCT/US98/07895) (UTFD:546P).

Liu et al., "The 40–kDa subunit of DNA fragmentation factor induces DNA fragmentation and chromatin condensation during apoptosis," *Proc. Natl. Acad. Sci. USA*, 95:8461–8466, 1998.

Mukae et al., "Molecular cloning and characterization of human caspase–activated DNase," *Proc. Natl. Acad. Sci. USA*, 95:9123–9128, 1998.

Wu et al., "Inhibition of Nf–kB/Rel induces apoptosis of murine B Cells," *EMBO J.*, 15:4682–4690, 1996.

Lee et al., "Involvement of histone hyperaceltylation in triggering DNA fragmentationof rat thymocytes undergoing apoptosis," *FEBS Lett.* 395:183–187, 1996.

Cai et al., "IkBalpha overexpression in human breast carcinoma NCF7 cells inhibits nuclear facotr–kB activation but not tumor necrosis factor–alpha–induced apoptosis," *J. Biol. Chem.*, 272:96–101, 1997.

Waring et al., "Apoptosis induced by gliotoxinis preceded by phosphorylation of histone H3 and enhaced sensitivity of chromatin to nuclease digestion,".

* cited by examiner

FIG. 1

Comparison of Human DFF40 and Mouse CAD

```
  1 MCAVLRQPKCVKLRALHSACKFGVAARSCQELLRKGCVRFQLPMPGSRLCLY  50
    :|..||:||||||:|: |||||:|||||:|||||:||||| .|||||||
  1    MLQKPKSVKLRALRSPRKFGVAGRSCQEVLRKGCLRFQLPERGSRLCLY  49

51 EDGTEVTDDCFPGLPNDAELLLLTAGETWHGYVSDITRFLSVFNEPHAGV  99
    |||||:|||:|..:|::|||:||| |:.|:|||||| ||||.|:||:.|:
 50 EDGTELTEDYFPSVPDNAELVLLTLGQAWQGYVSDIRRFLSAFHEPQVGL  99

100 IQAARQLLSDEQAPLRQKLLADLLHHVSQNITAETREQDPSWFEGLESRF 149
    ||||.|||:||||| ||:|||||||:|||||.||||.:||.|||||||||
100 IQAAQQLLCDEQAPQRQRLLADLLHNVSQNIAAETRAEDPPWFEGLESRF 149

150 RNKSGYLRYSCESRIRGYLREVSAYTSMVDEAAQEEYLRVLGSMCQKLKS 199
    ..||||||||||||:||||||.|.| |:..||||:|||||||||||:|:|
150 QSKSGYLRYSCESRIRSYLREVSSYPSTVGAEAQEEFLRVLGSMCQRLRS 199

200 VQYNGSYFDRGAEASSRLCTPEGWFSCQGPFDLESCLSKHSINPYGNRES 249
    :|||||||||.::|||||||||||||||||||::||||:|||||:|||||
200 MQYNGSYFDRGAKGGSRLCTPEGWFSCQGPFDMDSCLSRHSINPYSNRES 249

250 RILFSTWNLDHIIEKKRTVVPTLAEAI..QDGREVNWEYFYSLLFTAENL 297
    ||||||||||||||||||::|||.||| |||||:|||||:||||.|||
250 RILFSTWNLDHIIEKKRTIIPTLVEAIKEQDGREVDWEYFYGLLFTSENL 299

298 KLVHIACHKKTTHKLECDRSRIYRPQTGSRRKQPARKKRPARKRD      342
    |||||.|||||||||.||||:||.||||:||| :||||.||:.
300 KLVHIVCHKKTTHKLNCDPSRIYKPQTRLKRKQPVRKRQ            338
```

DNA FRAGMENTATION FACTOR INVOLVED IN APOPTOSIS

This is a divisional of application Ser. No. 09/061,702, filed Apr. 16, 1998, which issued as U.S. Pat. No. 6,165,737.

The government may own rights in the present invention pursuant to grant number GMRO1-55942 from the National Institutes of Health.

BACKGROUND OF THE INVENTION

1. Field of the Invention

The present invention relates generally to the field of molecular biology. More particularly, it concerns the discovery of a DNA fragmentation factor that triggers nuclear changes during apoptosis. Methods and compositions for making and using the same are disclosed.

2. Description of Related Art

Apoptosis, or programmed cell death, is executed through a "suicide" program that is built into all animal cells (reviewed by White, 1996; Wyllie, 1995). Cells undergoing apoptosis show distinctive morphological changes, including membrane blebbing, cytoplasmic and nuclear condensation, chromatin aggregation and formation of apoptotic bodies (Wyllie, 1980). The biochemical hallmark of apoptosis is the cleavage of chromatin into nucleosomal fragments (Wyllie et al., 1980). Multiple lines of evidence indicate that apoptosis can be triggered by the activation of a family of cysteine proteases with specificity for aspartic acid residues, including CED-3 of *C. elegans*, CPP32/Yama/Apopain of humans, and DCP-1 of Drosophila (Yuan et al., 1993; Xue et al., 1996; Femandes-Alnemri, et al., 1994; Tewari, et al., 1995; Nicholson, et al., 1995; Song, et al., 1997). Recently, these proteins have been designated as caspases (Alnemri et al., 1996).

The most intensively studied apoptotic caspase is caspase-3, previously called CPP32/Yama/Apopain (Fernandes-Alnemri, et al., 1994; Tewari, et al., 1995; Nicholson, et al., 1995). Caspase-3 normally exists in the cytosolic fraction of cells as an inactive precursor that is activated proteolytically when cells are signaled to undergo apoptosis (Schlegel et al., 1996; Wang et al., 1996). Multiple apoptotic signals, including serum withdrawal, activation of Fas, treatment with granzyme B, ionizing radiation, and a variety of pharmacological agents, activate caspase-3 (Chinnaiyan et al., 1996; Darmon, et al., 1996; Datta et al., 1996, 1997; Erhardt and Cooper, 1996; Hasegawa et al., 1996; Jacobsen et al., 1996; Martin et al., 1996; Schlegel et al, 1996).

A caspase-3-specific tetrapeptide inhibitor, Ac-DEVD-CHO, can abolish the ability of cytosol from apoptotic cells to induce apoptosis in normal nuclei and block the initiation of the cellular apoptotic program m response to apoptotic stimuli (Nicholson et al., 1995; Dubrez, et al., 1996; Jacobsen et al., 1996). Deletion of caspase-3 from the mouse genome through homologous recombination results in excessive accumulation of neuronal cells, owing to a lack of apoptosis in the brain (Kuida et al., 1996). Addition of active caspase-3 to normal cytosol activates the apoptotic program (Enari et al., 1996). These data indicate that caspase-3 is both necessary and sufficient to trigger apoptosis.

The identified substrates of caspase-3 include poly(ADP-ribose) polymerase (PARP) (Tewari et al., 1995; Nicholson et al., 1995), sterol-regulatory element binding proteins (SREBPs) (Wang et al., 1995; 1996), the U1 associated 70 kDa protein (Caciola-Rosen et al., 1996), D4GDI (Na et al., 1996), huntingtin (Goldberg et al., 1996), and the DNA-dependent protein Kinase (Casciola-Rosen et al., 1996; Song et al., 1996). It is not known whether the cleavage of any of these substrates plays a causal role in apoptosis.

Given that apoptosis is tightly regulated and has been linked to pathways that are dysregulated in a variety of diseases including cancer, it is important to identify mechanisms by which to control this process.

SUMMARY OF THE INVENTION

The present invention is directed towards the identification of factors involved in apoptosis. Thus in a preferred embodiment, there is provided an isolated polypeptide encoding a DFF40 DNA fragmentation factor. In particularly preferred embodiment, the DNA fragmentation factor has the amino acid sequence as set forth in SEQ ID NO:2. Also provided by the present invention is an isolated peptide having between about 10 and about 50 consecutive residues of a DFF40 DNA fragmentation factor. In certain defined aspects, the DNA fragmentation factor has an amino acid sequence of about 10 to about 50 consecutive residues of SEQ ID NO:2. In particular embodiments, the peptide is conjugated to a carrier molecule. In preferred embodiments, the carrier molecule is selected from the group consisting of KLH and BSA.

The present invention further provides a monoclonal antibody that binds immunologically to a DFF40 DNA fragmentation factor. In certain embodiments, the antibody does not bind immunologically to other human polypeptides. In particular embodiments, the antibody further comprises a detectable label. The detectable label may be selected from the group consisting of a fluorescent label, a chemiluminescent label, a radiolabel and an enzyme.

The present invention contemplates a hybridoma cell that produces a monoclonal antibody that binds immunologically to a DFF40 DNA fragmentation factor. In preferred aspects the antibody does not bind immunologically to other human polypeptides.

Also contemplated is a polyclonal antisera, antibodies of which bind immunologically to a DFF40 DNA fragmentation factor. In defined embodiments, the antisera may be derived from an animal other than a human.

Also provided by the present invention is an isolated nucleic acid comprising a region, or the complement thereof, encoding a DFF40 DNA fragmentation factor or an allelic variant thereof. In a preferred embodiment, the DFF40 DNA fragmentation factor is human. In other preferred embodiments, the DNA fragmentation factor has the amino acid sequence of SEQ ID NO:2. In other preferred embodiments, the nucleic acid sequence comprises the coding region having the sequence of SEQ ID NO:1 or the complement thereof. It is contemplated that the nucleic acid may be selected from the group consisting of genomic DNA, complementary DNA and RNA.

In particularly preferred embodiments, the nucleic acid is a complementary DNA and further comprises a promoter operably linked to the region, or the complement thereof, encoding the DNA fragmentation factor. In further embodiments, the nucleic acid further comprises a polyadenylation signal operably linked to the region encoding the DNA fragmentation factor. In still further embodiments, the nucleic acid farther comprises an origin of replication. In other aspects of this embodiment, the nucleic acid may be defined as a viral vector selected from the group consisting of retrovirus, adenovirus, herpesvirus, vaccinia virus and adeno-associated virus. In particularly preferred embodiments, the nucleic acid is packaged in a virus particle. In other alternative embodiments, the nucleic acid is packaged in a liposome.

The present invention further provides an isolated oligonucleotide of between about 15 and about 50 consecutive bases of a nucleic acid, or complement thereof, encoding a DFF40 DNA fragmentation factor. In preferred embodiments, the DNA fragmentation factor is human. In particularly preferred embodiments, the nucleic acid is the coding region of SEQ ID NO:1. In other preferred embodiments, the oligonucleotide is about 15 bases in length, is about 17 bases in length is about 20 bases in length is about 25 bases in length, is about 50 bases in length. Of course longer oligonucleotides also are contemplated.

Another aspect of the present invention provides a plasmid construct comprising a first nucleic acid encoding a DFF40 DNA fragmentation factor. In particular embodiments, the construct further comprises a first promoter active in eukaryotic cells positioned 5' to the first nucleic acid. In yet additional embodiments, the construct, further comprises a second nucleic acid encoding a DFF45 DNA fragmentation factor. In yet another embodiment the construct further comprises an internal ribosome entry site (IRES), wherein the IRES is positioned 3' to the upstream nucleic acid and 5' to the downstream nucleic acid. In other embodiments, the construct further comprises a second promoter functional in eukaryotic cells, wherein the second promoter is positioned 5' to the second nucleic acid.

It is contemplated that any promoter disclosed herein may be used, in particularly preferred aspects, the first promoter is selected from the group consisting of CMV IE, SV40 IE, RSV, β-actin, tetracycline regulatable and ecdysone regulatable. In other embodiment the second promoter is selected from the group consisting of CMV IE, SV40 IE, RSV, β-actin, tetracycline regulatable and ecdysone regulatable.

It is contemplated in certain embodiments of the present invention that the construct may further comprise a polyadenylation signal positioned 3' to the first nucleic acid. In other embodiments, the expression construct comprising (i) a first polyadenylation signal positioned 3' to the first nucleic acid and (ii) a second polyadenylation signal positioned 3' to the second nucleic acid. In particularly defined aspects, the polyadenylation signal may be from BGH, thymidine kinase or SV40. In particular aspects the expression construct is a viral vector. In more defined embodiments, the viral vector is selected from the group consisting of retrovirus, adenovirus, vaccinia virus, herpesvirus and adeno-associated virus.

The present invention also provides a method of inducing apoptosis in a cell comprising the step of providing the cell with a DFF40 DNA fragmentation factor, wherein the provision of the DFF40 to the cell results in apoptosis. In certain embodiments, the DFF40 is provided as a protein complex comprising a DFF45 DNA fragmentation factor, and wherein the DFF45 is altered, with respect to wild-type DFF45, such that it lacks anti-apoptotic function but retains DFF40-chaperone function. In other embodiments, the DFF40 is provided as a protein complex comprising a DFF45 DNA fragmentation factor, and further comprising causing the DFF45 to be cleaved. In particular embodiments, the cleavage is effected by increasing the activity of caspase 3. In other embodiments, the providing comprises contacting the cell with a first expression construct comprising a first nucleic acid encoding a DFF40 polypeptide and a promoter functional in eukaryotic cells wherein the first nucleic acid is under the control of the promoter.

In particular aspects of the present invention, the method may further comprise providing a factor selected from the group consisting of a histone, a high mobility group protein and a nuclear factor. In certain aspects of the present invention, the expression construct further comprises a second nucleic acid encoding a DFF45 polypeptide, and wherein the DFF45 is altered, with respect to wild-type DFF45, such that it lacks anti-apoptotic function but retains DFF40-chaperone function. More particularly, the expression construct further comprises an internal ribosome entry site (IRES), wherein the IRES is positioned 3' to the upstream nucleic acid and 5' to the downstream nucleic acid. In preferred aspects, the expression construct further comprises a second promoter functional in eukaryotic cells, wherein the second nucleic acid is under the control of the second promoter. Additional aspects of this embodiment contemplate that the complex is encapsulated in a liposome.

In additional preferred aspects of this embodiments, the method may further comprise providing to the cells a second expression construct comprising a second nucleic acid encoding a DFF45 polypeptide and a second promoter functional in eukaryotic cells wherein the second nucleic acid is under the control of the second promoter. In particularly defined embodiment, the cell is a tumor cell. In other defined embodiments, the tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue.

The present invention further provides a method for inhibiting the growth of a cancer cell comprising the step of contacting a cancer cell with a DNA fragmentation factor designated DFF40 under conditions permitting the uptake of the DNA fragmentation factor by the cell, wherein the presence of the DFF40 in the cell induces apoptosis. In particular embodiments, the inhibition of growth may be measured by reduced proliferation, reduced cell migration, increase in contact inhibition, reduction in soft agar growth or restoration of cell cycling. In other embodiments, the cancer cell is within a subject. In other more preferred embodiments, the subject is a human.

It is contemplated that the DFF40 may be provided as a protein complex comprising a DFF45 DNA fragmentation factor, and wherein the DFF45 is altered, with respect to wild-type DFF45, such that it lacks anti-apoptotic function but retains DFF40-chaperone function. In other embodiments the DFF40 is provided as a protein complex comprising a DFF45 DNA fragmentation factor, and further comprising causing the DFF45 to be cleaved. In defined embodiments the cleavage is effected by increasing the activity of caspase 3. In certain embodiments, the providing comprises contacting the cell with a first expression construct comprising a first nucleic acid encoding a DFF40 polypeptide and a promoter functional in eukaryotic cells wherein the first nucleic acid is under the control of the promoter. In certain preferred aspects, the expression construct may further comprise a second nucleic acid encoding a DFF45 polypeptide, and wherein the DFF45 is altered, with respect to wild-type DFF45, such that it lacks anti-apoptotic function but retains DFF40-chaperone function.

Another aspect of the present invention provides a method for treating cancer comprising the step of contacting a tumor cell within a subject with a nucleic acid (i) encoding a DFF40 DNA fragmentation factor and (ii) a promoter active in the tumor cell, wherein the promoter is operably linked to the region encoding the DNA fragmentation factor, under conditions permitting the uptake of the nucleic acid by the tumor cell.

Also contemplated is a method of identifying a modulator of DFF40 activity comprising the steps of providing a cell expressing a DFF40/DFF45 complex; contacting the cell with a candidate substance; activating DFF40; and comparing the apoptosis of the cell in step (iii) with the apoptosis observed when the candidate substance is not added, wherein an alteration in apoptosis indicates that the candidate substance is a modulator the apoptotic activity. The cell may be a tumor cell. In particular embodiments, the apoptosis is measured using a parameter selected from the group consisting of DNA fragmentation, DNA condensation, DFF40 expression, nuclease activation, caspase activation, and DFF cleavage.

It is contemplated that the candidate substance independently may be a chemotherapeutic or radiotherapeutic agent. The candidate substance may also be selected from a small molecule library. In other embodiments, the candidate substance is a protein. In still further embodiment the candidate substance is a DFF45 analogue. In other embodiments the candidate substance may be a high mobility group (HMG) protein analogue. In defined aspects the HMG protein independently may be HMG-1, HMG-2, HMG-14 or an analogue thereof. In other embodiments the candidate substance is a nuclear factor. It is also contemplated that the candidate substance is an histone.

The present invention further contemplates a modulator of apoptotic activity identified according to a method comprising the steps of (i) providing a cell expressing a DFF401/DFF45 complex; (ii) contacting the cell with a candidate substance; (iii) activating DFF40; and (iv) comparing the apoptosis of the cell in step (iii) with the apoptosis observed when the candidate substance is not added, wherein an alteration in apoptosis indicates that the candidate substance is a modulator the apoptotic activity.

Also contemplated is an isolated DNA fragmentation factor complex for regulating chromatin stability, the complex comprising a DFF40 polypeptide and a DFF45 polypeptide. In preferred embodiment, the DFF40 subunit has the sequence of as set forth in SEQ ID NO:2. In other embodiments the DFF45 subunit has the sequence of as set forth in SEQ ID NO:4.

Another embodiments of this invention contemplates a method of producing a functional DNA fragmentation factor comprising providing to a cell a first nucleic acid encoding a DFF40 polypeptide; and a second nucleic acid encoding a DFF45 polypeptide; and expressing the complex in a cell, wherein the coexpression of the polypeptides allows for the formation of a functional DFF40 polypeptide. It is contemplated that the method may further comprise the step of causing the DFF45 polypeptide to be cleaved by caspase 3. In preferred embodiments, the first and the second nucleic acids are contained in the same expression construct and both are under the control a first promoter. In denied aspects the first and the second nucleic acids are contained in different expression constructs and are under the control a first and a second promoter, respectively. In additional embodiments, the second nucleic acid encodes a DFF45 polypeptide that is altered, with respect to wild-type DFF45, such that it lacks anti-apoptotic function but retains DFF40-chaperone function.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Comparison of amino acid sequences of human DFF40 and mouse CAD. A cDNA clone encoding human DFF40 was obtained as described in Example 1. The amino acid sequences of human DFF40 and mouse CAD (Enari et al., 1998); Sakahira, et al., 1998) are aligned by the Lipman-Pearson method of the DNASTAR program. The proteolytic peptide sequences from purified DFF40 are underlined. A putative nuclear localization signal at the carboxyl terminus of DFF40 is boxed. The amino acid residues are numbered on the left and right.

DESCRIPTION OF ILLUSTRATIVE EMBODIMENTS

1. The Present Invention

The present invention, for the first time, identifies a DNA fragmentation factor that plays a central role in triggering apoptosis. The sequence of the human DFF40 protein (SEQ ID NO:2) has been deduced from its cDNA sequence (SEQ ID NO:1). DFF40 is a novel protein that possesses about 71% homology to a previously identified mouse CAD (Enari et al., 1998; Sakahira, et al., 1998). DFF40 further comprises a putative nuclear localization signal similar to that previously noticed in the C-terminal of CAD (Enari et al., 1998; Sakahira, et al., 1998).

Previously, the inventors have shown that DFF is a heterodimeric protein comprising a 40 kDa subunit and a 45 kDa subunit (Liu et al., 1997). The inventors have shown herein that expression of recombinant DFF induces DNA fragmentation. cDNAs encoding DFF45 and DFF40 were expressed either individually or together by transfection into human embryonic kidney 293 cells. It was found that neither DFF40 nor DFF45 expressed alone exhibited a significant increase in DNA fragmentation activity when incubated with nuclei compared with a vector control. However, when both proteins were co-expressed, there was a dramatic increase in DFF activity. This activity of recombinant DFF was dependent on caspase-3. Thus, there appears to be a requirement for co-expression of both DFF subunits for activity to occur and when such co-expression is present, the DFF activity requires the presence of a caspase-3 activity.

The inventors have further demonstrated that the DFF activity is localized to the nuclear fraction. DFF45 is therefore like other nuclear substrates of caspase-3 such as poly(ADP-ribose) polymerase and lamins that are cleaved as the result of nuclear translocation of active caspases (Kaufmann et al., 1993; Lazebnik, et al., 1995). The presence of any DFF in the cytosol is attributed to nuclear leakage during homogenization. Such nuclear leakage during homogenization also has been previously observed for other nuclear proteins (Paine et al., 1983).

Latent DFF, containing both 40 and 45 kDa subunits, becomes activated when DFF45 is cleaved by caspase-3 (Lui et al., 1997). Since co-expression of both DFF40 and DFF45 seems to be required to generate functional recombinant DFF, an *E. coli* double-expression plasmid was engineered to contain both DFF40 and DFF45 cDNAs. This double expression plasmid generated functional DFF. The recombinant DFF thus produced induced DNA fragmentation when incubated with nuclei in the presence of caspase-3. Furthermore, inhibition of caspase-3 blocked this activity.

From investigations designed to determine the mechanism of DFF activation and to identify the active component of DFF after activation, the inventors determined that the fractions that exhibited constitutive DFF activity consisted of only the 40 kDa subunit, indicating that DFF40 is the active form of DFF. This was further confirmed by western blot analysis using an antibody generated against DFF40 recombinant protein The fragments of DFF45 generated by caspase-3 cleavage did not associate with DFF activity.

Additional characterization of the DFF40 fragment showed that active DFF induced DNA fragmentation in co-incubated nuclei without a further requirement for caspase-3. This activity was insensitive to the caspase-3 inhibitor. Thereafter, the activated, pure DFF40 was designated as A-DFF40. These data definitively prove that DFF40 is the active component that induces DNA fragmentation.

Without co-expression of DFF45, however, DFF40 produced in either mammalian cells or insect cells does not have fragmentary activity. DFF45, therefore, seems to mediate the correct folding of DFF40, but is not the component of the final functional structure of A-DFF40. Therefore, DFF45 appears to act as a molecular chaperone (Hartl et al., 1994). However, unlike the general molecular chaperones Hsp70 and Hsp60 (Hartl et al., 1994), DFF45 remains complexed with DFF40, keeping it from being active until a specific signal is received, in this case the activation of caspase-3. Such a specific molecular chaperone provides a double safety control to prevent unwanted activation of DFF.

First of all, such an arrangement prevents newly synthesized DFF40 from cleaving DNA. Since DFF40 is translocated to nuclei, imbalanced expression of DFF45 and DFF40 could otherwise have a catastrophic effect on the cells by introducing chromatin condensation and fragmentation. Only the DFF40 that is complexed with DFF45 has the potential to generate active DFF. Secondly, by forming a complex with DFF40, DFF45 also prevents DFF40 from activating its DNase activity. In this way, only the DFF heterodimer that is cleaved by caspase-3 will become active. In this sense, DFF45 also is an inhibitor for DFF40. Similar observations have been made for the CAD/ICAD system in mice (Enari et al., 1998; Sakahira et al., 1998).

Purified DFF shows little nuclease activity in the presence of caspase-3 when incubated directly with naked DNA compared to incubation with nuclei (Lui et al., 1997). However, DNase activity may be detectable in the presence of a relatively crude system as indicated for CAD (Enari et al., 1998; Sakahira, et al., 1998). Thus, the inventors investigated the likelihood that additional protein(s) were required to generate a nuclease activity that cleaved chromatin DNA at the inter-nucleosomal linker regions during apoptosis. In doing so, the inventors identified and purified a protein from HeLa cell nuclear extracts. Protein sequencing analysis revealed that this protein was the high mobility group (HMG) protein-2. Further, the inventors found that other chromatin associated proteins, histone H1, and other HMG proteins such as HMG-1, HMG-2 and HMG-14 stimulated the DNase activity of DFF40 when incubated with purified plasmid DNA while the core histones and bovine serum albumin (BSA) showed little effects.

A-DFF40 manifests its intrinsic DNase activity only when high concentrations of A-DFF40 are used; little DNase activity is detected at lower concentrations unless histone H1 is present. The stimulatory effect of histone H1 was more than 10-fold. The finding that abundant chromatin-associated proteins, such as HMG-1, HMG-2, and histone H1 can markedly stimulate the intrinsic DNase activity of DFF40 suggests that rather than passively cleaving chromatin DNA at the linker region because of its greater accessibility to nuclease, DFF-dependent DNase is targeted directly to the nucleosomal linker region of chromatin where the HMG proteins and histone H1 are known to be located (Jackson, 1979; Peters, 1979; Schroter and Bode, 1982).

In addition, since histone H1 and HMGs also are believed to be involved in organizing high order chromatin structure (Jackson, 1979; Peters, 1979; Schroter and Bode, 1982), these proteins also may facilitate A-DFF40 DNase to disassemble these high order chromatin structures. Such a model would provide a more efficient way to disassemble complex chromatin DNA into nucleosomes as compared to disassembly by random cleavage of DNA. Given the teachings of the present invention, the molecular mechanism by which chromatin-associated proteins stimulate A-DFF40 DNase activity in apoptosis now can be studied.

Accordingly, the present invention, provides a gene responsible for triggering an apoptotic response in humans. With the gene in hand, it now becomes possible to exploit the information encoded by the gene in a variety of apoptosis related applications. As shown herein, the DFF polypeptides of the present invention can regulate chromatin stability and hence provide important regulators of cell viability. The polypeptides may be produced recombinantly from transformed host cells from the DFF encoding nucleic acids or purified from mammalian cells. The invention provides isolated DFF hybridization probes and primers capable of specifically hybridizing with the disclosed DFF gene. Also provided are DFF-specific binding agents such as specific antibodies. Other embodiments provide methods of making and using the subject compositions in diagnostic application for example to provide genetic hybridization screens for DFF transcripts. Therapeutic applications in which gene therapy to modulate DFF gene expression or to induce an apoptotic response also are contemplated. Further, the DFF polypeptides disclosed herein have uses in the biopharmaceutical industry as immunogens, reagents for isolating other transcriptional regulators and as reagents for screening chemical libraries for lead pharmacological agents. Methods and compositions for use in these and other applications are discussed in greater detail herein below.

2. The DNA Fragmentation Factor

According to the present invention, there has been identified a gene encoding the active subunit of the human DNA fragmentation factor, designated herein as DFF40. This molecule is capable of inducing apoptosis in various cell types. The term "apoptosis" is well-known to those of skill in the art. Examples of other apoptotic genes include p53, members of the Bcl family, such as Bax, Bak, Bcl-$X_s$, Bik, Bid, Bad, Harakiri, AdE1b and ICE-CED3 protease. While these molecules are structurally distinct, they form a group of functionally-related molecules, of which DFF40 is a member. The uses in which these other apoptosis mediators now are being exploited are equally applicable to DFF40. Further, it is contemplated that DFF may be used in combination with these other apoptotic genes to mediate apoptosis in, for example, cancer cells.

For the functional expression of DFF40 further DFF activity is required. This activity is presented by DFF45, which acts as a molecular chaperone to direct the folding of DFF40. Therefore, in the cytoplasm, DNA fragmentation factor is found as DFF40/DFF45 complex. Human DFF45 has been cloned by the present inventors and has a nucleic acid sequence as shown in SEQ ID NO:3. The coding region of the DFF45 gene encodes a DFF45 protein of SEQ ID NO:4. All the DNase activity is associated with DFF40, however, and the DFF activity only occurs once the DFF40 complexed with DFF45 is cleaved to generate separate DFF40 and DFF45 subunits. DFF45 appears to act as a molecular chaperone to facilitate the appropriate folding of DFF40 and also appears to act as an inhibitor for DFF40.

In addition to the entire DFF40 and DFF45 molecules, the present invention also relates to fragments of the polypeptide that may or may not retain the apoptotic (or other) activity of DFF40 and inhibitory or molecular chaperone activity of DFF45. Fragments, including the N-terminus of the molecule may be generated by genetic engineering of translation stop sites within the coding region (discussed below). Alternatively, treatment of the DFF40 or DFF45 molecule with proteolytic enzymes, known as proteases, can produce a variety of N-terminal, C-terminal and internal fragments. Examples of fragments may include contiguous residues of the DFF40 and DFF45 sequences given in SEQ ID NO:2 and SEQ ID NO:4, respectively, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

a. Structural Features of the Polypeptide

The gene for DFF40 encodes a 339 amino acid polypeptide. The predicted molecular weight of this molecule is 40 kDa. DFF45 encodes the molecular chaperone for DFF40 and has a molecular weight of 45 kDa. Thus, at a minimum, these molecules may be used as standards in assays as a molecular weight marker.

It also should be mentioned that the C-terminus of the DFF40 molecule shows some homology to a nuclear localization domain.

b. Functional Aspects

When the present application refers to the function of DFF40 or "wild-type" activity, it is meant that the molecule in question has the ability to induce DNA fragmentation. Other activities that are attributable the normal DFF40 gene product are binding DFF45, DNase activity, induction of apoptosis, activation of caspase-3 and chromatin condensation. Determination of which molecules possess this activity may be achieved using assays familiar to those of skill in the art.

When the present application refers to the function of DFF45 or "wild-type" activity, it is meant that the molecule in question has the ability to specifically bind to the DFF40 subunit of DFF. Thus in one sense this molecule has the ability to inhibit the apoptotic action of DFF40. Determination of which molecules possess this activity may be achieved using assays familiar to those of skill in the art.

As stated above, there is an indication that DFF40 also comprises a nuclear localization domain. The portion of the protein located at C-terminal of the protein and is a perfect match for the conserved nuclear localization domain of CAD (Enari et al., 1998).

c. Variants of DFF40 and DFF45

Amino acid sequence variants of the polypeptide can be substitutional, insertional or deletion variants. Deletion variants lack one or more residues of the native protein which are not essential for function or immunogenic activity. A common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

A particular aspect of the present invention contemplates generating DFF45 mutants for use in combination with the DFF40 protein of the present invention to allow for the DFF40 to fold correctly but not inhibit the DFF40 function. Also contemplated are mutants of DFF40 that do not require the presence of DFF45 to aid in the activation of DFF40's apoptotic activity.

In particular aspects it is contemplated that the particular mutants of the DFF45 peptide will retaining its molecular chaperone capabilities, but lack its apoptotic function. In order to construct such mutants, one of skill in the art will employ standard technologies well known to those of skill in the art. Specifically contemplated will be N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Proteins expressed from such mutant can be assayed for apoptosis inhibiting and/or chaperone function as described throughout the specification. Similar techniques are employed in internal deletion mutants, however, in internal deletion mutants are generated by using two suitably placed restriction sites, thereby allowing a precisely defined deletion to be made, and the ends to be religated as above.

Also contemplated are partial digestions mutants. In such instances one of skill in the art would employ a "frequent cutter", that cuts the DNA in numerous places depending on the length of reaction time. Thus, by varying the reaction conditions it will be possible to generate a series of mutants of varying size, which may then be screened for activity.

An random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

Once general areas of the gene are identified as encoding particular protein domains, point mutagenesis may be employed to identify with particularity which amino acid residues are important in particular activities associated with DFF45. Thus one of skill in the art will be able to generate single base changes in the DNA strand to result in an altered codon and a missense mutation.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+30±1); glutamate (+3.0±1); serine (+0.3); asparagine (+2.0); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of DFF40, but with altered and even improved characteristics.

d. Domain Switching

As described in the examples, the present inventors have identified the human DFF40 and DFF45, there exists at least one set of putative homologs for these proteins. The mouse CAD protein, described by Enari et al. (1998), has 71% homology with DFF40. In addition, given the teachings of the present invention, mutations may be identified in DFF40 which may alter its function. Similarly, the mouse ICAD protein can be considered homologous to DFF45 (Enari et al. 1998). These studies are potentially important for at least two reasons. First, they provide a reasonable expectation that still other homologs, allelic variants and mutants of this gene may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule. One way in which this information can be exploited is in "domain switching."

Domain switching involves the generation of chimeric molecules using different but, in this case, related polypeptides. By comparing the mouse, and human sequences for CAD and DFF40 respectively with the DFF40-like proteins of other species, and with mutants and allelic variants of these polypeptides, one can make predictions as to the functionally significant regions of these molecules. Of course the same applies for DFF45 and ICAD. It is possible, then, to switch related domains of these molecules in an effort to determine the criticality of these regions to DFF40 and DFF45 function. These molecules may have additional value in that these "chimeras" can be distinguished from natural molecules, while possibly providing the same function Based on the sequence identity, at the amino acid level, of the mouse, and human sequences, it may be inferred that even small changes in the primary sequence of the molecule will affect function. Further analysis of mutations and their predicted effect on secondary structure will add to this understanding.

e. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Fusion to a polypeptide that can be used for purification of the substrate-DFF40 complex would serve to isolated the substrate for identification and analysis. Similarly, DFF45 fusion peptides can also be studied.

Examples of such fusion protein expression systems are the glutathione S-transferase (GST) system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). The present inventor has made fusion of GST-DFF40 and 6×HIS-DFF40 for purification purposes.

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation.

A particularly useful fusion construct may be one in which a DFF40 peptide is fused to a DFF45 peptide in such a way to yield an active complex. By an "active complex" it is meant that the DFF40 part of the fusion construct comprise an active apoptotic activity while the DFF45 part of the fusion construct comprises the molecular chaperone aspect of the DFF45 without having a DFF40 inhibitory capacity. Such a stable construct will be useful in that it can be provided to a cell in an active stable form, without requiring any additional caspase activation.

In still further systems, it is possible to create fusion protein constructs to enhance immunogenicity of a DFF40 fusion construct to increase immunogenicity are well known to those of skill in the art, for example, a fusion of DFF40 or DFF45 with a helper antigen such as hsp70 or peptide sequences such as from Diptheria toxin chain or a cytokine such as IL2 will be useful in eliciting an immune response. In other embodiments, fusion construct can be made which will enhance the targeting of the DFF40 (and/or DFF45) related compositions to a specific site or cell. For example, fusing DFF40 or a DFF40 type protein to a ligand will be an effective means to target the composition to a site expressing the receptor for such a ligand. In this manner the DFF40 or DFF40 related (and/or DFF45) composition may be delivered into a cell via receptor mediated delivery. The protein, be it DFF40 or DFF45, can be attached covalently or fused to a ligand. This can be used as a mechanics for delivery into a cell. The ligand with the protein attached may then be internalized by a receptor bearing cell.

Other fusion systems produce polypeptide hybrids where it is desirable to excise the fusion partner from the desired polypeptide. In one embodiment, the fusion partner is linked to the recombinant DFF polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In further embodiments, the gene sequences encoding the DFF40 and DFF45 polypeptides may first be analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially $E.$ $coli$, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not, therefore, prove useful in vivo or in situ studies. Deletion of transmembrane-encoding sequences from the genes used for expression can be achieved by standard techniques. For example, fortuitously-placed restriction enzyme sites can be used to excise the desired gene fragment, or PCR™-type amplification can be used to amplify only the desired part of the gene.

f. Purification of Proteins

It will be desirable to purify DFF40, DFF45 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.). A particularly preferred affinity chromatography used in the present invention is nickel affinity chromatography.

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

g. Synthetic Peptides

The present invention also relates to smaller DFF40 and DFF45-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

U.S. Pat. No. 4,554,101 (incorporated herein by reference) also teaches the identification and preparation of epitopes from primary amino acid sequences on the basis of hydrophilicity. Through the methods disclosed in Hopp, one of skill in the art would be able to identify epitopes from within any amino acid sequence encoded by any of the DNA sequences disclosed herein.

h. Antigen Compositions

The present invention also provides for the use of DFF40 proteins or peptides, as well as DFF45 proteins and peptides, as antigens for the immunization of animals relating to the production of antibodies. It is envisioned that either DFF40, DFF45, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

3. Nucleic Acids

The present invention also provides, in another embodiment, a gene encoding DFF40. The gene for the human DFF40 molecule have been identified. Similarly, the inventors have also identified the gene for human DFF45. The present invention is not limited in scope to the particular gene or genes identified herein, however, as one of ordinary skill in the art could, using the nucleic acids corresponding to the DFF40 or DFF45 gene, readily identify related homologs in various other species (e.g., rat, rabbit, monkey, gibbon, chimp, ape, baboon, cow, pig, horse, sheep, cat and other species). The finding that there exists a mouse homolog for this gene makes it likely that other species more closely related to humans will, in fact, have a homolog as well.

In addition, it should be clear that the present invention is not limited to the specific nucleic acids disclosed herein. As discussed below, a "DFF40 or DFF45 gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of DFF40 or DFF45.

a. Nucleic Acids Encoding DFF

The human DFF40 gene is disclosed in SEQ ID NO:1, and the human DFF45 gene is disclosed in SEQ ID NO:3. Nucleic acids according to the present invention may encode an entire DFF40 gene, a domain of DFF40 that expresses an apoptosis inducing activity, a DFF45 binding function, or any other fragment of the DFF40 sequences set forth herein. Similarly, other nucleic acids of the present invention may encode the entire DFF45 gene, a domain of DFF45 that expresses an apoptosis inhibitory effect on DFF40 activity, a DFF40 binding function, a DFF45 molecular chaperone function or any other fragment of the DFF45 sequences set forth herein.

The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given DFF40 or DFF45 from a given species may be represented by natural variants that have slightly different nucleic acid sequences but, nonetheless, encode the same protein (see Table 1 below).

As used in this application, the term "a nucleic acid encoding a DFF40 or DFF45" refers to a nucleic acid molecule that has been isolated free of total cellular nucleic acid. In preferred embodiments, the invention concerns a nucleic acid sequence essentially as set forth in SEQ ID NO:1 and SEQ ID NO:3, respectively. The term "as set forth in SEQ ID NO:1 and SEQ ID NO:3" means that the nucleic acid sequences substantially correspond to a portion of SEQ ID NO:1 and SEQ ID NO:3. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1." Sequences that are essentially the same as those set forth in SEQ ID NO:1 may also be functionally defined as sequences that are capable of hybridizing to a nucleic acid segment containing the complement of SEQ ID NO:1 under standard conditions.

The DNA segments of the present invention include those encoding biologically functional equivalent DFF40 proteins and peptides and biological equivalents of DFF45 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

b. Oligonucleotide Probes and Primers

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3 (for DFF40 and DFF45, respectively) under relatively stringent conditions such as those described herein. Such sequences may encode the entire DFF40 or DFF45 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 2800 or 2839 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

One method of using probes and primers of the present invention is in the search for genes related to DFF40 or DFF45, more particularly, homologs of the proteins from other species. The existence of murine homologs for both proteins strongly suggest that other homologs of the human DFF40 and DFF45 will be discovered in species more closely related, and perhaps more remote, than mouse. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

c. Antisense Constructs

In some cases, mutant apoptotic genes may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of DFF40 or DFF45 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozymes) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

d. Ribozymes

Another approach for addressing the "dominant negative" mutant phenotype is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

4. Vectors for Cloning, Gene Transfer and Expression

Within certain embodiments expression vectors are employed to express the DFF40, the DFF45 polypeptide product or both, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide.

a. Regulatory Elements i. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ 3system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic Virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 2).

TABLE 2

Tissue specific promoters

| Tissue | Promoter |
| --- | --- |
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim., 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, radiation-inducible (e.g., EGR (Joki et al., 1995)), Alpha-inhibin, RNA pol III tRNA met and other amino acid promoters, U1 snRNA (Bartlett et al., 1996), MC-1, PGK, β-actin and α-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

ii. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be; used in combination with the nucleic acid encoding a gene of interest in an expression construct (Table 3 and Table 4). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 3

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 4

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |

TABLE 4-continued

| Element | Inducer |
| --- | --- |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

iii. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

iv. IRES

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (poliovirus and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

b. Delivery of Expression Vectors

There are a number of ways in which expression vectors may introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). Delivery mechanisms are discussed in further detail herein below.

i. Viral Transfer

Adenovirus. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide, a protein, a polynucleotide (e.g., ribozyme, or an mRNA) that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retroviruses, the adenoviral infection of host cells does not result in chromosomal integration because adenoviral DNA can replicate in an episomal manner without potential genotoxicity. As used herein, the term "genotoxicity" refers to permanent inheritable host cell genetic alteration. Also, adenoviruses are structurally stable, and no genome rearrangement has been detected after extensive amplification of normal derivatives. Adenovirus can infect virtually all epithelial cells regardless of their cell cycle stage. So far, adenoviral infection appears to be linked only to mild disease such as acute respiratory disease in non-immunosuppressed humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

The E3 region encodes proteins that appears to be necessary for efficient lysis of Ad infected cells as well as preventing TNF-mediated cytolysis and CTL mediated lysis of infected cells. In general, the E4 region encodes is believed to encode seven proteins, some of which activate the E2 promoter. It has been shown to block host mRNA transport and enhance transport of viral RNA to cytoplasm. Further the E4 product is in part responsible for the decrease in early gene expression seen late in infection. E4 also inhibits E1A and E4 (but not E1B) expression during lytic growth. Some E4 proteins are necessary for efficient DNA replication however the mechanism for this involvement is unknown. E4 is also involved in post-transcriptional events in viral late gene expression; i.e., alternative splicing of the tripartite leader in lytic growth. Nevertheless, E4 functions are not absolutely required for DNA replication but their lack will delay replication. Other functions include negative regulation of viral DNA synthesis, induction of sub-nuclear reorganization normally seen during adenovirus infection, and other functions that are necessary for viral replication, late viral mRNA accumulation, and host cell transcriptional shut off.

In a current system, recombinant adenovirus is generated from homologous recombination between shuttle vector and provirus vector. Possible recombination between the proviral vector and Ad sequences in 293 cells, or in the case of pJM17 plasmid spontaneous deletion of the inserted pBR322 sequences, may generate full length wild-type Ad5 adenovirus. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993; Jones and Shenk, 1978).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical, medical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression investigations (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993), intranasal inoculation (Ginsberg et al., 1991), aerosol administration to lung (Bellon, 1996) intra-peritoneal administration (Song et al., 1997), Intra-pleural injection (Elshami et al., 1996) administration to the bladder using intra-vesicular administration (Werthman, et al., 1996), Subcutaneous injection including intraperitoneal, intrapleural, intramuscular or subcutaneously) (Ogawa, 1989) ventricular injection into myocardium (heart, French et al., 1994), liver perfusion (hepatic artery or portal vein, Shiraishi et al., 1997) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome However, new packaging cell lines are now available that should greatly decrease the likelihood of recombination (Markowitz et al., 1988; Hersdorffer et al., 1990).

Herpesvirus. Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transducing factor (Post et al., 1981; Batterson and Roizman, 1983; Campbell et al., 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

Adeno-Associated Virus. Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et a., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al., 1997a). Until recently, AAV was believed to infect almost all cell types, and even cross species barriers. However, it now has been determined that AAV infection is receptor-mediated (Ponnazhagan an et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al. (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

Vaccinia Virus. Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

ii. Non-viral Transfer

There are a number of alternatives to viral transfer of genetic constructs. This section provides a discussion of methods and compositions of non-viral gene transfer.

DNA constructs of the present invention are generally delivered to a cell, and in certain situations, the nucleic acid or the protein to be transferred may be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EFGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

c. Cell Culture and Selection Methods

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

5. Generating Antibodies Reactive with DFF

In another aspect, the present invention contemplates an antibody that is immunoreactive with a DFF40 molecule or a DFF45 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention Polyclonal antisera may be obtained, after allowing time for antibody generation, simply by bleeding the animal and preparing serum samples firm the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to DFF40 or the DFF45-related antigen epitopes. Additionally, it is proposed that monoclonal antibodies specific to the particular DFF40 or DFF45 of different species may be utilized in other useful applications.

In general, both polyclonal and monoclonal antibodies against DFF40 or DFF45 may be used in a variety of embodiments. For example, they may be employed in antibody cloning protocols to obtain cDNAs or genes encoding other DFF40 or DFF45 proteins. They may also be used in inhibition studies to analyze the effects of DFF40 and/or DFF45 related peptides in cells or animals. Anti-DFF40 and anti-DFF45 antibodies will also be useful in immunolocalization studies to analyze the distribution of DFF40 and DFF45 during various cellular events, for example, to determine the cellular or tissue-specific distribution of DFF40 and DFF45 polypeptides under different points in the cell cycle. A particularly useful application of such antibodies is in purifying native or recombinant DFF40 or DFF45, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified DFF40 and/or DFF45 protein, polypeptide or peptide or cell expressing high levels of DFF40 and/or DFF45. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63-Ag8, P3-X63-Ag8-653, NS1/1/Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

6. Diagnosing Disorders Involving DFF

It may be possible that alterations in DFF40 and/or DFF45 are associated with a diseased state. Therefore, DFF40 and the corresponding gene and the DFF45 and the corresponding gene may be employed as a diagnostic or prognostic indicator of such a disorder. Such a disorder will be defined as any disorder that results from a dysregulation of apoptosis caused by an aberration in DFF40 and/or DFF45 expression or function. More specifically, point mutations, deletions, insertions or regulatory perturbations relating to DFF may cause cancer or promote cancer development, cause or promoter tumor progression at a primary site, and/or cause or promote metastasis.

a. Genetic Diagnosis

One embodiment of the instant invention comprises a method for detecting variation in the expression of DFF40 and/or DFF45. This may comprises determining that level of DFF40 and/or DFF45 or determining specific alterations in the expressed product. Obviously, this sort of assay has importance in the diagnosis of related diseased states.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have DFF40-related or DFF45-related pathologies. In this way, it is possible to correlate the amount or kind of DFF40 (or DFF45) detected with various clinical states. Various types of defects have been identified in this manner. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of protein produced, both by altering the transcription of the gene or in destabilizing or otherwise altering the processing of either the transcript (mRNA) or protein.

It is contemplated that mutations in the DFF40 and or DFF45 gene may be identified in accordance with the present invention. A variety of different assays are contemplated in this regard, including but not limited to, fluorescent in situ hybridization (FISH; Pinkel et al., 1986, U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

l. Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemilluminescent (luciferase).

ii. Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carring out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89101025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, M. A., In: *PCR™ PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al. (1989), incorporated herein by reference in its entirety.

iii. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

iv. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

v. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the DFF40 or DFF45 gene that may then be analyzed by direct sequencing.

vi. Kit Components

All the essential materials and reagents required for detecting and sequencing DFF40 and/or DFF45 and variants thereof may be assembled together in a kit. This generally will comprise preselected primers and probes. Also included may be enzymes suitable for amplifying nucleic acids including various polymerses (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

vii. Design and Theoretical Considerations for Relative Quantitative

RT-PCR™ Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

viii. Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

b. Immunodiagnosis

Antibodies of the present invention can be used in characterizing the DFF40 and/or DFF45 content of healthy and diseased tissues, through techniques such as ELISAs and Western blotting. This may provide a screen for the presence or absence of malignancy or as a predictor of future disease.

The use of antibodies of the present invention, in an ELISA assay is contemplated. For example, anti-DFF40 (or anti-DFF45) antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for DFF40 (or DFF45) that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 250 to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

7. Screening for Modulators of Apoptosis

The present invention also contemplates the use of DFF40, DFF45, DFF complexes and active fragments thereof in the screening of compounds that modulate (increase or decrease activity) of DFF40. These assays may make use of a variety of different formats and may depend on the kind of "activity" for which the screen is being conducted. Contemplated functional "read-outs" include binding to DFF, DFF40 or DFF45; DFF, DFF40 or DFF45 binding to a substrate; DNA condensation activity; DNA fragmentation activity; caspase activation; association of DFF40 with DFF45; cleavage of DFF45; and apoptosis, growth, metastasis or cell division.

a. Assay Formats

J. Stimulators of Apoptosis

The present invention provides methods of screening for stimulators of apoptosis by monitoring apoptosis in the presence and absence of the candidate substance and comparing such results. It is contemplated that this screening technique will prove useful in the general identification of a compound that will serve the purpose of promoting, augmenting or increasing the apoptosis of cell. Such compounds will be useful in the treatment of various disorders resulting from impaired apoptosis, such as for example, cancer, autoimmune disease, neurodegenerative disorders, strokes and the like.

In these embodiments, the present invention is directed to a method for determining the ability of a candidate substance to stimulate the apoptosis of cells that either naturally express DFF complex or have been engineered to express DFF complex as described herein. The method including generally the steps of:

(i) providing a cell expressing a DFF40/DFF45 complex;

(ii) contacting said cell with a candidate substance;

(iii) activating DFF40; and (iv) comparing the apoptosis of the cell in step (iii) with the apoptosis observed when said candidate substance is not added, wherein an alteration in apoptosis indicates that said candidate substance is a modulator of said apoptotic activity.

To identify a candidate substance as being capable of stimulating apoptosis in the assay above, one would measure or determine the apoptosis in the absence of the added candidate substance. One would then add the candidate substance to the cell and determine the apoptosis in the presence of the candidate substance. A candidate substance which increases the apoptosis or capacity relative to apoptosis observed in its absence is indicative of a candidate substance with stimulatory capability.

ii. Inhibitors of Apoptosis

These assays may be set up in much the same manner as those described above in assays for apoptosis stimulators. In these embodiments, the present invention is directed to a method for determining the ability of a candidate substance to have an inhibitory or even antagonistic effect on apoptosis in cells The method including generally the steps of:

(i) providing a cell expressing a DFF40/DFF45 complex;

(ii) contacting said cell with a candidate substance;

(iii) activating DFF40; and (iv) comparing the apoptosis of the cell in step (iii) with the apoptosis observed when said candidate substance is not added, wherein an alteration in apoptosis indicates that said candidate substance is a modulator of said apoptotic activity.

To identify a candidate substance as being capable of inhibiting apoptosis, one would measure or determine apoptosis in the absence of the added candidate substance. One would then add the candidate inhibitory substance to the cell and determine the apoptosis in the presence of the candidate inhibitory substance. A candidate substance which is inhibitory would decrease the apoptosis, relative to the amount of apoptosis in its absence.

iii. Candidate Substances

As used herein the term "candidate substance" refers to any molecule that is capable of modulating apoptosis. The candidate substance may be a protein or fragment thereof, a small molecule inhibitor, or even a nucleic acid molecule. In certain embodiments herein, the inventors have found that DFF45 acts as an inhibitor of DFF40 DNase activity and histone-1 and HMG proteins act as stimulators of such activity. It may prove to be the case that the most useful pharmacological compounds for identification through application of the screening assay will be compounds that are structurally related to other known modulators of apoptosis. The active compounds may include fragments or parts of naturally-occurring compounds or may be only found as active combinations of known compounds which are otherwise inactive. However, prior to testing of such compounds in humans or animal models, it will be necessary to test a variety of candidates to determine which have potential.

Accordingly, the active compounds may include fragments or parts of naturally-occurring compounds or may be found as active combinations of known compounds which are otherwise inactive. Accordingly, the present invention provides screening assays to identify agents which stimulate or inhibit cellular apoptosis, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known stimulators or inhibitors of apoptosis.

The candidate screening assays are simple to set up and perform. Thus, in assaying for a candidate substance, after obtaining a cell expressing functional DFF40, one will admix a candidate substance with the cell, under conditions which would allow measurable apoptosis to occur. In this fashion, one can measure the ability of the candidate substance to stimulate the apoptosis of the cell in the absence of the candidate substance. Likewise, in assays for inhibitors after obtaining a cell expressing functional DFF40, the candidate substance is admixed with the cell. In this fashion the ability of the candidate inhibitory substance to reduce, abolish, or otherwise diminish apoptosis mediated by DFF40 from said cell may be detected.

"Effective amounts" in certain circumstances are those amounts effective to reproducibly stimulate apoptosis from the cell in comparison to their normal levels. Compounds that achieve significant appropriate changes in activity will be used.

Significant changes in apoptosis, e.g., as measured using DNA fragmentation, DNA condensation, biological activity and the like are represented by an increase/decrease in apoptosis of at least about 30%–40%, and most preferably, by changes of at least about 50%, with higher values of course being possible. The active compounds of the present invention also may be used for the generation of antibodies which may then be used in analytical and preparatory techniques for detecting and quantifying further such inhibitors.

It will, of course, be understood that all the screening methods of the present invention are useful in themselves notwithstanding the fact that effective candidates may not be found. The invention provides methods for screening for such candidates, not solely methods of finding them.

b. In vitro Assays

In one particular embodiment, the invention encompasses various binding assays. These can include screening for inhibitors of DFF complexes or for molecules capable of binding to DFF40, as a substitute of the chaperone function of DFF45. In such assays, DFF40 or a fragment thereof may be either free in solution, fixed to a support, expressed in or on the surface of a cell. Either the polypeptide or the binding agent may be labeled, thereby permitting determination of binding.

Such assays are highly amenable to automation and high throughput. High throughput screening of compounds is described in WO 84/03564. Large numbers of small peptide test compounds are synthesized on a solid substrate, such as plastic pins or some other surface. The peptide test compounds are reacted with DFF40 and washed. Bound polypeptide is detected by various methods. Combinatorial methods for generating suitable peptide test compounds are specifically contemplated.

Of particular interest in this format will be the screening of a variety of different DFF45 mutants. These mutants, including deletion, truncation, insertion and substitution mutants, will help identify which domains are involved with the DFF40/DFF45 interaction. Once this region has been determined, it will be possible to identify which of these mutants, while retaining chaperone function, do not inhibit the apoptotic activity of DFF40.

Purified DFF40 or a binding agent can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the DFF40 active region to a solid phase.

Other forms of in vitro assays include those in which functional readouts are taken. For example cells in which a wild-type or mutant DFF complex or active DFF40 polypeptide are expressed can be treated with a candidate substance. In such assays, the substance would be formulated appropriately, given its biochemical nature, and contacted with the cell. Depending on the assay, culture may be required. The cell may then be examined by virtue of a number of different physiologic assays, as discussed above. Alternatively, molecular analysis may be performed in which the cells characteristics are examined. This may involve assays such as those for protein expression, enzyme function, substrate utilization, mRNA expression (including differential display of whole cell or polyA RNA) and others.

c. In Vivo Assays

The present invention also encompasses the use of various animal models. Here, the identity seen between human and mouse DFF40 provides an excellent opportunity to examine the function of DFF40 in a whole animal system where it is normally expressed. By developing or identifying mice with aberrant DFF functions (overexpression of DFF, constitutively activated DFF, DFF negative), one can provide models that will be highly predictive of disease in humans and other mammals, and helpful in identifying potential therapies.

Another form of in vivo model is an animal with a hyperproliferative disorder (such as cancer). In this model, the hyperproliferative tissue is treated with DFF40 in combination with other agents to determine the effect on DFF40 function in vivo. Similarly, in tissues exhibiting DFF40-related abnormal cell senescence or cell death, it is possible to treat with a candidate substance to determine whether the DFF40 activity can be down-regulated in a manner consistent with a therapy.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

d. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for DFF40 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have activity as stimulators, inhibitors, agonists, antagonists of DFF40 or molecules affected by DFF40 function, such as caspase-3 or DFF45. Such rational drug design may start with lead compounds identified by the present invention including histone-1 and HMG proteins (e.g. HMG-1, HMG-2 and HMG-14). By virtue of the availability of cloned DFF40 and DFF45 sequences, sufficient amounts of these proteins can be produced to perform crystallographic studies. In addition, knowledge of the polypeptide sequences permits computer employed predictions of structure-function relationships.

8. Methods for Treating Disease States

The present invention deals with the treatment of disease states that involve hyperproliferative disorders including benign and malignant neoplasias. Such disorders include restinosis, cancer, multi-drug resistant cancer, primary, psoriasis and metastatic tumors, angiogenesis. The types of disease that may be treated, according to the present invention, is limited only by the involvement of DFF40 in the induction of apoptosis in a cancer cell. By involvement, it is not even a requirement that DFF40 be mutated or abnormal—the expression or overexpression of this apoptotic gene may be sufficient actually overcome kill, inhibit or otherwise abrogate the growth of the cell. In particular, it is contemplated that a wide variety of tumors may be treated using DFF40 therapy, including cancers of the brain (glioblastoma, astrocytoma, oligodendroglioma, ependymomas), lung, liver, spleen, kidney, lymph node, pancreas, small intestine, blood cells, colon, stomach, breast, eadometrium, prostate, testicle, ovary, skin, head and neck, esophagus, bone marrow, blood or other tissue.

In many contexts, it is not necessary that the completely kill all the cells in a tumor, it will be sufficient to induce enough "apoptosis" to accomplish a meaningful treatment, so that for example, tumor growth is slowed or tumor size is decreased to some degree. It may be that the tumor growth is completely blocked, however, or that some tumor regression is achieved. Clinical terminology such as "remission" and "reduction of tumor" burden also are contemplated given their normal usage.

a. Genetic Based Therapies

One of the therapeutic embodiments contemplated by the present inventors is the intervention, at the molecular level, in the events involved in the apoptosis of some cancers. Specifically, the present inventors intend to provide, to a cancer cell, an expression construct capable of providing DFF40 to that cell in a functional form. Because the sequence homology between the human, and mouse genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way DFF40 and DFF45 may be utilized according to the present invention.

b. Protein Therapy

Another therapy approach is the provision, to a subject, of DFF40 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

c. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that DFF40 therapy to induce apoptosis in a cancer cell could be used similarly in conjunction with chemo- or radiotherapeutic intervention. It also may prove effective to combine DFF40 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a DFF40 and/or DFF45 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either DFF40 (alone or in conbination with DFF45) or the other agent will be desired. Various combinations may be employed, where DFF40 (alone in an active form or in combination with DFF45) is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. A useful composition to deliver to a cell would be a composition comprising a DFF40/DFF45 complex. The combination of this complex with a composition that will activate the complex, for example, caspase 3 or an effector that increases the activity of caspase will be effective in delivering an apoptotic phenotype to a cell. Of note, it is known that radiation and or chemotherapy activates caspase-3, as such delivering a DFF40/DFF45 complex to cancer cells undergoing such treatment will be useful in inducing apoptosis in such cells.

Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with an expression construct, as described above.

Agents that directly cross-link nucleic acids, specifically DNA, are envisaged to facilitate DNA damage leading to a synergistic, antineoplastic combination with DFF40. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors also are contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of DFF40 (and/or DFF45) expression constructs to patients will be a very efficient method for delivering a therapeutically effective gene to counteract a clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining DFF-targeted therapies with chemo- and radiotherapies, it also is contemplated that combination with other gene therapies will be advantageous. For example, targeting of DFF40 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by themselves in treating a DFF40 related abnormality. In this regard, reference to chemotherapeutics and non-DFF40 gene therapy in combination should also be read as a contemplation that these approaches may be employed separately.

e. Formulations and Routes for Administration to Patients

Where clinical applications are contemplated, it will be necessary to prepare the viral expression vectors of the present invention as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may be administered via any suitable route, including parenterally or by injection. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, in accordance with the present methods, viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{11}$, $10^{12}$, $10^{13}$ or $10^{14}$ pfu. Particle doses may be somewhat higher (10 to 100-fold) due to the presence of infection defective particles.

In this connection, sterile aqueous media which can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In a preferred embodiment, the present invention is directed at the treatment of human malignancies. A variety of different routes of administration are contemplated. For example, a classic and typical therapy will involve direct, intratumoral injection of a discrete tumor mass. The injections may be single or multiple; where multiple, injections are made at about 1 cm spacings across the accessible surface of the tumor. Alternatively, targeting the tumor vasculature by direct, local or regional intra-arterial injection are contemplated. The lymphatic systems, including regional lymph nodes, present another likely target given the potential for metastasis along this route. Further, systemic injection may be preferred when specifically targeting secondary (i.e., metastatic) tumors.

In another embodiment, the viral gene therapy may precede or following resection of the tumor. Where prior, the gene therapy may, in fact, permit tumor resection where not possible before. Alternatively, a particularly advantageous embodiment involves the prior resection of a tumor (with or without prior viral gene therapy), followed by treatment of the resected tumor bed. This subsequent treatment is effective at eliminating microscopic residual disease which, if left untreated, could result in regrowth of the tumor. This may be accomplished, quite simply, by bathing the tumor bed with a viral preparation containing a unit dose of viral vector. Another preferred method for achieving the subsequent treatment is via catheterization of the resected tumor bed, thereby permitting continuous perfusion of the bed with virus over extended post-operative periods.

9. Transgenic Animals/Knockout Animals

In one embodiment of the invention, transgenic animals are produced which contain a functional transgene encoding wild-type or mutant DFF40 or DFF45 polypeptides. Transgenic animals expressing DFF transgenes, recombinant cell lines derived from such animals and transgenic embryos may be useful in methods for screening for and identifying agents that induce or repress function of DFF40 or DFF45. Transgenic animals of the present invention also can be used as models for studying indications of abnormal DFF40 or DFF45 expression.

In one embodiment of the invention, a DFF transgene is introduced into a non-human host to produce a transgenic animal expressing a human or murine DFF40 and/or DFF45 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous DFF40 (and/or DFF45) by homologous recombination between the transgene and the endogenous gene; or the endogenous gene may be eliminated by deletion as in the preparation of "knock-out" animals. Typically, a DFF40 (and/or DFF45) gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress DFF40 or express a mutant form of the polypeptide. Alternatively, the absence of a DFF40 in "knock-out" mice permits the study of the effects that loss of DFF40 protein has on a cell in vivo. Knock-out mice also provide a model for the development of DFF40-related abnormalities.

As noted above, transgenic animals and cell lines derived from such animals may find use in certain testing experiments. In this regard, transgenic animals and cell lines capable of expressing wild-type or mutant DFF40 may be exposed to test substances. These test substances can be screened for the ability to enhance wild-type DFF40 (and/or DFF45) expression and/or function or impair the expression or function of mutant DFF40 (and/or DFF45).

10. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials

Ac-Tyr-Val-Ala-Asp-aldehyde (Ac-YVAD-CHO) was obtained from Biothem & Bioscience Inc.; Ac-Asp-Glu-Ala-Asp-aldehyde. (Ac-DEAD-CHO) as described in (Wang et al, 1995); Protease K and DNase free RNase A from Worthington; Coomassie Brilliant Blue, Molecular weight standards for SDS-PAGE and gel filtration chromatography from Bio-Rad; Protein concentrations were determined by the Bradford method; General molecular biology methods were as in Sambrook et al. HeLa cell cytosol was prepared as described (Liu et al., 1996b).

Assay for DNA Fragmentation Factor (DFF)

Caspase-3 was prepared as described in (Liu et al., 1996a). The purified enzyme was stored in Buffer A (20 mM Hepes-KOH, pH 7.5, 10 mM KCl, 1.5 mM MgCl, 1 mM sodium EDTA, 1 mM sodium EGTA, 1 mM DTT, and 0.1 mM PMSF) containing 20% glycerol and 1 mg/ml bovine serum albumin (BSA) in multiple aliquots at −80° C. Hamster liver nuclei were prepared as described in (Liu et al., 1996b); HeLa cell nuclei and nuclear extract were prepared as in (Wang et al., 1993). Purified nuclei were resuspended in buffer B (10 mM PIPES, pH 7.4, 80 mM KCl, 20 mM NaCl, 5 mM sodium EGTA, 250 mM sucrose, and 1 mM DTT) at $8.5 \times 10^7$ nuclei/ml and stored in multiple aliquots at −80° C. The DNA fragmentation was assayed by incubating an aliquot (7 ml) of hamster liver or HeLa cell nuclei and 6 ml of caspase-3 with the indicated enzyme fractions at 37° C. for 2 hr in a final volume of 60 ml adjusted with buffer A. After incubation, 330 ml of buffer C (100 mM Tris-HCl, pH 8.5, 5 mM EDTA, 0.2 M NaCl, 0.2% w/v SDS, and 0.2 mS/ml proteinase K) was added to each reaction and incubated at 37° C. overnight. NaCl was then added to a final concentration of 1.5 M and the nuclear debris was spun down for 15 min in a microcentrifuge at room temperature. The DNA in the supernatants were precipitated with equal volume of 100% ethanol. The DNA precipitate was washed once with 70% (v/v) ethanol and resuspended in 40 ml of buffer D (10 mM Tris-HCl, pH 7.5, 1 mM sodium EDTA and 200 rag/ml DNase-free RNase A). After incubation at 37° C. for 2 hr, the DNA was loaded onto a 2% agarose gel and electrophoresis was conducted at 50 V for 2 hr in 0.5×Tris-Borate-EDTA CfBE) buffer (1×TBE buffer contains 90 mM Tris-Borate/2 mM EDTA). The gel was stained with 2 mS/ml ethidium bromide for 15 min, destained with water for 1 hr, and visualized under UV light.

Purification of DFF from HeLa S-100

All purification steps were carried out at 4° C. All chromatography steps except the Sepharose column and the phenyl-Sepharose column were carried out using an automatic fast protein liquid chromatography (FPLC) station [Pharmacia]

750 ml of HeLa S-100 from 100 liter of suspension cultured HeLa cells were applied to a SP-Sepharose calm (200 ml bed volume) equilibrated with buffer A. The column was washed with three column volumes of buffer A and eluted with two column volumes of buffer A containing 0.5 mM NaCl. Ammonium sulfate (1 M) was added directly to the SP-Sepharose 0.5 M eluate. After rotating at 4° C. for 1 hr, the sample were centrifuged at 15,000 rpm for 30 min in a Sovall IA-600 rotor. The supernate was directly loaded onto a 100 ml phenyl Sepharose column equilibrated with buffer A containing 1 M ammonium sulfate and 0.5 M NaCl. The column was washed with three bed volumes of buffer A containing 1 M ammonium sulfate and 0.5 M NaCl and the bound material was eluted with two bed volumes of buffer A. Ammonium sulfate was added to the phenyl Sepharose eluate to 50% saturation. After stirring at 4° C. for 5 hr, the sample was centrifuged at 15,000 rpm for 15 min in a Sovall JA-600 rotor. The pellet was resuspended in buffer A and loaded onto a Superalex-200 16/60 gel filtration column (Pharmacia) equilibrated with buffer A and eluted with the same buffer. Fractions of 4 ml were collected and assayed for DFF activity. The active fractions from the gel filtration column were pooled and loaded onto a MonoS 10/10 column (Pharmacia) equilibrated with buffer A. The column was washed with 50 ml of buffer A and eluted with a 200 ml 0–0.2 M linear NaCl gradient. Fractions of 4 ml were collected and assayed for DFF activity. The active fractions from the MonoS column were pooled and loaded onto a 1 ml hydroxyapatite column (Bio-Pad) equilibrated with buffer A. The column was washed with 10 ml of buffer A and the bound material was eluted, with 0–0.25 M linear phosphate gradient. 1 ml fractions were collected and assayed for DFF activity. The active fraction was pooled and loaded onto a Mono Q 5/5 column (Pharmacia) equilibrated with buffer A. The column was washed with 10 ml of buffer A containing 0.1 M NaCl and DFF was eluted from the column with a 30 ml 0.1–0.3 M linear NaCl gradient. Fractions of 1 ml were eluted and assayed for DFF activity.

Western Blot Analysis

A monoclonal antibody against bureau PARP (c-2–10) was used as described in (Kaufmanu et al, 1993). A monoclonal antibody against human lamin B1 was from Calbiochem. Anti-DFF-45 anti-serum was generated by immunizing rabbits with a recombinant DFF45 fusion protein (see below). Immunoblot analysis was performed with the horseradish peroxidase conjugated goat anti-mouse (PARP and lamin B.1) or goat anti-rabbit (DFF45) immunoglobulin G using Enhanced Chemiluminescence western blotting detection reagents (Amersham).

Biotinylation of DFF

The biotinylation of DFF was carried out using a ECL protein biotinylation kit (Amersham) with modifications. Briefly, 0.6 mg of purified DFF was incubated with 10 ml of biotinylation reagent in 120 ml of 40 mM bicarbonate buffer at room temperature for 1 hr. Then 20 ml of 1 M Tris-HCl (pH 8.0) was added to the reaction followed by incubation at room temperature for 1 hour. The sample was then dialyzed again in buffer F (20 mM Tris-HCl, pH 7.5, 10 mM KCl. 1.5 mM MgCl2, 1 mM sodium EDTA, 1 mM sodium. EGTA, 1 mM DTT, 1 mM PMSF) at 4° C. overnight.

cDNA Cloning of DFF45

HeLa poly(A)+-mRNA was purified using Rapid mRNA Purification kit (Pharmacia). First-strand cDNA synthesis was carried out using a First Strand cDNA Synthesis kit with oligo(dT) primers (Pharmacia). The cDNA was amplified with 40 pmol oligonucleotides designed from an EST clone (#116412) that encodes one of the DFF45 peptide sequence. A 395 bp PCRproduct was subcloned into the PCR H vector using the TA cloning kit (Invitrogen) and sequenced. The 395 bp PCR product was subsequently labeled with [$^{32}$P] dCTP using, redi prime RANDOM Primer Labeling kit (Amersham) and used to screen a Hela 1 gtl 1 cDNA library by hybridizing duplicate filter at 42° C. for 3 hr in Rapid-hyb buffer (Amersham). The filters were washed twice wither 1× saline citrate (SSC)/0.1% SDS for 15 min at room temperature and once with 0.5×SSC/0.1% SDS for 10 min at 65° C. Out of 8×10$^5$ plaques screened, a 1.3 kb partial length clone was identified and subcloned into the EcoRI site of PCRII vector (In VitroGene). A 1.0 lob EcoRIf BamHI fragment was excised from 5' end of the 1.3 kb insert and labeled with dCTP as described above. A Hela 1 Exlox library (Yokoyama et al., 1993) was screened with this 1 kb cDNA fragment as described above. In 6×10$^5$ plaques screened, 30 positive clones were identified. A 1.6 kb clone which contain the longest open reading frame was sequenced in both strands in an automated sequence.

cDNA Cloning of DFF40

To clone the cDNA of DFF40, 1 ml (10$^8$ pfu) aliquot of 1 Exlox HeLa cDNA library (Yokoyama et al., 1993) was heated at 99° C. for 20 min. to release the DNA contents which were directly amplified with 300 pmol of forward primer 5'-GAGGTIGAI(T/C)(G/A)IGA(A/G)TA(T/C)TT(T/C)TA(T/C)GG-3' (SEQ ID NO:5 designed according to EVDWEYFYG (SEQ ID NO:19 in FIG. 1) and 40 pmol SP6 reverse primer 5'-ATTTAGGTGACACTATAGAA-3' (SEQ ID NO:6, on the arm of the vector) using the PCR reaction with 30 cycles of 94° C. for 1 min.; 50° C. for 1 min.; and 72° C. for 1 min. The PCR product was purified by passing a PCR purification column (Qiagen). 1/50 of the purified product was further amplified using 300 pmol of forwarding primer 5'-GA(A/G)TA(T/C)TT(T/C)TA(T/C)GGI(T/C)TI(T/C)TITT(C/T)AC-3' (SEQ ID NO:7, corresponding to EYFYGLLFT (SEQ ID NO:20) in FIG. 1) and 300 pmol of reverse primer 5'-GT(T/C)TG(T/A/G/C)GG(T/C)TT(A/G)TA(A/G/T)AT-3' (SEQ ID NO:8, corresponding to peptide IYKPQT, (SEQ 1D NO:21) in FIG. 1) in a PCR reaction as described above. A 132 bp PCR product was obtained and sequenced after subcloning into a PCR 2.1 vector using the TA cloning kit (Invitrogen). Based on the sequence of this 132 bp fragment, a nesting PCR was performed with 30 cycles of 94° C. for 1 min.; 55° C. for 1 min.; and 72° C. for 1 min. using 1 ml of cDNA library as template as described above. The first round of PCR was carried out using a forward primer 5'-TCAGAGAACCTAAAACTAGTGCACATTGTC-3' (SEQ ID NO:9) and a Sp6 reverse primer as described above. The PCR product was purified by passing through a PCR purification column (Qiagen). 1/50 of the purified product was amplified again using a forward primer 5'-TGCCATAAGAAAACCACCCACAAGCTCAAC-3' (SEQ ID NO:10) and a Sp6 reverse primer as described above. A 250 bp PCR product was obtained and labeled with a-$^{32}$P-dCTP using a redi prime RANDOM Primer kit (Amersham) and used to screen the HeLa 1 Exlox cDNA library by hybridizing the duplicate filter at 42° C. overnight in Rapid-hyb buffer (Amersham). The filters were washed twice with 1× saline citrate (SSC)/0.1% SDS for 10 min. at 65° C. Out of 6×10$^5$ plaques screened, 14 positive clones were identified and the longest 2.8 kb clone that contains the entire open reading frame was sequenced in both strands in an automated sequencer.

Production of DFF-45 Fusing Protein

Primers were designed to PCR-amplify the DFF-45 cDNA open reading frame and the amplified cDNA was subcloned inframe into the NdeI/XheI sites of the bacterial expression vector pET-15b (Novagen). The expression plasmid was transformed into bacteria BL21(DE3). In a typical DFF-45 preparation, a 10 ml overnight cultured bacteria containing DFF-45 expression vector was added into a 500 ml LB broth, cultured for 3 hr. by shaking at 220 rpm in 37° C., and then isopropyl-1-thio-B-D-galactopyranoside (IPTG) was added to a final concentration of 1 mM and cultured for another 2 hr. The bacterial pellet was resuspended in 10 ml of buffer A and broken by sonication. After centrifugation at 4,000 g for 15 min; the supernatant was loaded onto a nickel affinity column (6 ml). The column was washed with 30 ml buffer A containing 1 M NaCl followed by 20 ml of Buffer A. The column was eluted with Buffer A containing 250 mM imidazole. About 10 mg DFF45 protein was purified from a 500 ml culture.

Expression of DFF in 293 Cells

To express DFF in 293 cells, a flag tag was engineered at the carboxyl terminal of DFF40 by PCR amplifying the 2.8 kb cDNA containing the entire coding region of DFF40 using primers 5'-ATCCGATAT CATGCTCCAGAAGCCCAAGAGC-3' (SEQ ID NO:11) and 5'-ATCCCTCGAGTCACTTGTCGT CGTCGTCCT-TGTAGTCCTGGCGTTTCCGCACA GGCTG-3' (SEQ ID NO:12). The PCR fragment was subcloned into the EcoR V and XhoI sites of a pcDNA3 vector (Invitrogen) digested with the same restriction enzymes. The resulting plasmid was designated pDFF40-flag. The 1.5 kb cDNA encoding the entire coding region of DFF45 was subcloned into the NotI or EcoRI sites of a pcDNA3 vector (Invitrogen) and the resulting plasmid was designated pDFF45. The plasmids were prepared using a Qiagen Mega plasmid kit. Human embryonic kidney 293 cells were set up at 1×10$^6$ per 100-mm dish in medium A (Dulbecco's modified eagle's medium containing 100 u/ml of penicillin and 100 μg/ml of streptomycin sulfate) supplemented with 10% (v/v) fetal calf serum and grown in monolayer at 37° C. in an atmosphere of 5% CO$_2$. After incubation for 24 hr, each dish was transfected with either 20 mg vector alone, or 10 mg pDFF40-flag plus 10 mg vector, or 10 mg pDFF45 plus 10 mg vector, or 10 mg pDFF40-flag plus 10 mg pDFF45 using a MBS Transfection Kit (Stategene) as described (Zou et al., 1997). After 24 hr, the cells were harvested and the S-100 fractions were prepared as described (Liu et al., 1996). The assay for DFF was performed as described (Liu et al., 1997).

Immunostaining

Immunostaining of simian CV-1 cells was carried out as described in Luo and Sawadogo (1996). Briefly, simian CV-1 cells were transfected with 10 mg of pDFF45 plus 10 mg of pcDNA3 vector, or pDFF40-flag plus 10 mg of pcDNA3 vector, or 10 mg of pDFF45 plus 10 mg of DFF40-flag by the calcium phosphate precipitation method. 24 hr after transfection, CV-1 cells were washed three times in phosphate-buffered saline (PBS) and fixed for 10 min. in freshly prepared 3% paraformaldehyde in PBS. After washing three times in PBS, the cells were incubated in 0.15% Triton X-100 in PBS followed by washing in PBS for three times. The cells were then blocked for 60 min. in PBS containing 2% bovine serum albumin followed by incubation with anti-flag antibody or anti-DFF45 antibody at 1:1000 dilution for 4 hr. After washing with PBS for 10 min. for 3 times, the cells were then incubated with fluorescein-5-isothiocyanate (FITC) conjugated goat anti-rabbit (For DFF45) IgG (1:1000) or goat anti-mouse (for DFF40) IgG (1:1000). The cells were washed three times with PBS before being examined under a fluorescence microscope.

Plasmid Expression of DFF45 and DFF40

Expression of DFF45 and DFF40 in one plasmid was done in principle as described (Khokhlatchev et al., *J. Biol. Chem.*, 272:11957, 1997). Two primers 5'-CCCCTCTAGAATAGAAGGAGATATGCTCCAGAA GCCCAAGAGC-3' (SEQ ID NO:13) and 5'-ATCCCTCGAGTCAATGATGATGATGATGATGCT GGCGTTTCCGCACAGGCTG-3' (SEQ ID NO:14) were used to PCR amplify the coding region of DFF40 cDNA. The resulting 1 kb DNA fragment was subcloned into the XbaI and XhoI sites of the bacterial expression vector pET-15b (Novagene) and the resulting plasmid was designated pET-15b-DFF40His. To subclone DFF45 into pET-15b-DFF40His, primers 5'-ATCCCTCGAGGAA GGAGATATGGAGGTGACCG GGGACGCC-3' (SEQ ID NO:15) and 5'-AGAATACTCGAGCTATGTGGGAT CCTGT CTGGC-3' (SEQ ID NO:16) were used to PCR-amplify the coding region of DFF45 and the resulting DNA fragment was digested with XhoI and ligated into pET-15DFF40His digested with the same restriction enzyme. The expression plasmid containing both DFF45 and DFF40 was transformed into bacteria BL21(pLysS) (Novagene). In a typical DFF preparation, a 5 ml overnight culture of bacteria containing the DFF40/DFF45 expression vector was inoculated into 500 ml LB broth and the culture was incubated at 37° C. for 4 hr with shaking at 220 rpm. IPTG was added to the culture in a final concentration of 1 mM and continued shaking for another four hr. The bacteria were centrifuged and the pellet was resuspended in 20 ml buffer A containing 10 mg/ml pepstatin. After sonication, the sample was centrifuged at 10,000 g for 30 min. and the supernatant was loaded onto a 2 ml nickel affinity column. The column was washed with 500 ml Buffer A containing 1 M NaCl followed by 50 ml Buffer A and eluted with Buffer A containing 250 mM imidazole. The eluate from nickel affinity column was loaded onto a MonoS 5/5 column (Pharmacia) equilibrated with buffer A. The column was washed with 10 ml buffer A and eluted with a 30 ml 0–0.3 M linear NaCl gradient. About 0.2 mg of DFF was purified from 500 ml culture.

Antibody Production

Anti-DFF40 anti-serum was generated by immunizing rabbits with a recombinant DFF-40 fusion protein generated as described below. The primers 5'-GACATCTCATATGCTCCAGAAGCCCAAGAG-3' (SEQ ID NO:17) and 5'-GTCAGGCCTCGAGCAAAGACCAGGACGTGG-3' (SEQ ID NO:18) were designed to PCR-amplify the DFF40 cDNA from the 2.8 kb clone and the amplified 1.0 kb fragment encoding the entire protein sequence of DFF40 was subcloned in-frame into the NdeI/XhoI sites of the bacteria expression vector pET-15b (Novagen). The expression plasmid was transformed into bacteria BL21(DE3). In a typical DFF40 preparation, a 5 ml overnight cultured bacteria containing the DFF40 expression vector was added into 1 liter of LB broth with ampicillin and cultured for 3 hr by shaking at 220 rpm in 37° C. Isopropyl-1-thio-b-D-galactopyranoside (IPTG) was added to the culture in a final concentration of 1 mM and cultured for another 2 hr. The bacteria were harvested by centrifugation and the pellet was resuspended in 10 ml of buffer B (6 M GuHCL, 0.1 M sodium phosphate, 0.01 M Tris-HCl, pH 8.0). After centrifugation at 10,000 g for 15 mm., the supernatant was loaded onto a nickel affinity column (2 ml). The column was washed with 20 ml buffer C (8 M urea, 0.1 M sodium phosphate, 0.01 M Tris-HCl, pH 8.0) and eluted with Buffer C containing 250 mM imidazole. About 10 mg DFF40 protein was obtained from 1 liter of bacteria culture.

Example 2

Identification and Characterization of DFF45

Identification of DFF

To elucidate the molecular events leading to DNA fragmentation, an in vitro DNA fragmentation assay was set up in which normal nuclei from hamster liver were incubated with active recombinant caspase-3 together with Hela cell S-100 cytosol. Caspase-3 alone was not able to induce DNA fragmentation in the co-incubated nuclei; neither were the HeLa cell cytosolic or nuclear extracts. However, when caspase-3 and the HeLa S-100 fraction were incubated together with the nuclei, DNA fragmentation occurred. These data indicate the existence of a DNA fragmentation factor(s) (DFF) in HeLa cell cytosol which induces DNA fragmentation in the presence of caspase-3. No DFF activity was detected in the nuclear extract.

Purification of DFF

Using caspase-3-dependent DNA fragmentation as an assay, DFF was purified from HeLa cell S400 in an eight-step procedure (Table 5 and Example 1).

TABLE 5

Purification of DFF from HeLa cells

| Step | Fraction | Protein mg | Specific Activity units/mg | Total Activity unit | Purification-fold | Recovery % |
|---|---|---|---|---|---|---|
| 1 | S-100 | 3750 | 526 | 1972500 | | 100 |
| 2 | SP-Sepharose | 968 | 1466 | 1419355 | 2.8 | 72 |
| 3 | Phenyl-Sepharose | 275 | 3040 | 835820 | 5.8 | 42 |
| 4 | 50% Ammonium Sulfate Precipitation | 88 | 8333 | 733333 | 16 | 37 |
| 5 | Superdex-200 | 20 | 34285 | 685714 | 65 | 35 |
| 6 | Mono S | 0.675 | 227920 | 153846 | 433 | 7.8 |
| 7 | Hydroxyapatite | 0.2 | 65789 | 65789 | 625 | 3.3 |
| 8 | Mono Q | 0.015 | 4000000 | 60000 | 7604 | 3.0 |

DFF activity eluted from a Mono Q column, the last step of the purification, at about 250 mM NaCl. These fractions were subjected to SDS-PAGE followed by Coomassie Brilliant Blue staining. Two polypeptides with molecular masses of 45 kDa and 40 kDa were observed to co-elute with the DFF activity. The Coomassie stain was used because the 45 kDa protein stained poorly with silver. No other proteins were detected in fraction containing the peak of DFF activity.

Purified DFF from the Mono Q column induced DNA fragmentation in co-incubated nuclei in a fashion that was dependent on its concentration and the concentration of caspase-3. As increasing amounts of purified DFF were added to the reaction, the extent of DNA fragmentation increased as demonstrated by the increase in the intensity of small size nucleosomal DNA fragments (~180 base pair/nucleosome) and the decrease of large molecular weight genomic DNA. At the highest concentration used, almost all the DNA was cleaved into the size of single nucleosomes after 2 hr. No DNA fragmentation was observed when caspase-3 was omitted from the reaction A similar pattern, although not as linear, was observed when increasing amounts of caspase-3 were added to the reactions with a fixed mount of DFF. Interestingly, DFF plus caspase-3 showed no detectable nuclease activity when incubated with naked phage DNA.

The relative linear increase in single nucleosomal fragments in response to increasing concentrations of DFF enabled us to quantitatively estimate the degree of purification of DFF. Table 5 shows estimates of the quantitative parameters for the purification of DFF starting with S-100 fraction from 100 liters of suspension cultured HeLa cells. The DFF was purified more than 7,000-fold to apparent homogeneity through the Mono Q step with an overall recovery of 3% activity.

To confirm the association of the 45-kDa and 40 kDa polypeptides, the purified DFF from the Mono Q column step was applied to a Superdex-200 gel-filtration column (Pharmacia). The column fractions were collected and assayed for DFF activity. DFF activity appeared at fractions 8 and 9 with an estimated molecular mass of 85 kDa relative to the molecular weight standard. The same fractions were also subjected to SDS-PAGE followed by Coomassie Blue staining and the 45-kDa and 40-kDa polypeptides were observed to co-elute with DFF activity.

Characterization of DFF

Several known substrates of caspase-3 are nuclear proteins, including PARP, lamin B1, 70 kD U1 RNP protein and DHA-dependent kinase. To test the possibility that the function of DFF is to facilitate the transport of caspase-3 into nuclei, the time course of cleavage of lamin B1 by caspase-3 was studies in the absence or presence of DFF, and found that caspase-3 alone was not able to induce DNA fragmentation. In the presence of DFF, nuclear DNA started to fragment alter 15 min of incubation and the extent of fragmentation increased with time. However, the rate of lamin B1 cleavage by caspase-3 remained the same with or without DFF. These data indicate that caspase-3 cuts the nuclear substrate with or without DFF. The same conclusion was obtained when the rate of cleavage of PARP was measured.

DFF Functions Downstream of Caspase-3

The inventors also determined whether caspase-3 was needed for DNA fragmentation after it had activated DFF, or whether the sole requirement for caspase-3 is to activate DFF. To distinguish these possibilities, a caspase-3 specific tetrapeptide aldehyde inhibitor, Ac-DEAD-CHO (Wang et al., 1995) was employed. Incubation of caspase-3 and DFF together induced DNA fragmentation, while caspase-3 or DFF alone failed to do so. When Ac-DEAD-CHO was included in the reaction, DNA fragmentation was inhibited, demonstrating that activation of DFF requires active caspase-3. Under the same conditions, the ICE specific inhibitor, Ac-DEAD-CHO, did not inhibit DNA fragmentation. In contrast, when caspase-3 and DFF were pre-incubated for 2 hr. followed by the addition of nuclei and Ac-DEAD-CHO, them was no longer inhibition of DNA fragmentation reaction. These data indicate that caspase-3 activity is no longer required for DNA fragmentation once DFF is activated.

The above protocol also provided an opportunity to determine whether the cleavage of nuclear substrates by caspase-3, such as PARP and Lamin B1, are necessary for DNA fragmentation. It had not been clear whether the cleavage of PARP or Lamin is a required step for DNA fragmentation, To directly test this requirement, purified DFF was pre-incubated with caspase-3 and then nuclei were added in the presence of Ac-DEAD-CHO, or the control inhibitor Ac-DEAD-CHO. Neither Ac-DEAD-CHO nor Ac-DEAD-CHO had any effect on DNA fragmentation when added after DFF and caspase-3 had been pre-incubated. However, Ac-DEAD-CHO still blocked the cleavage of both PARP and lamin B1 in the co-incubated nuclei. These data indicate that DNA fragmentation does not require cleavage of nuclear substrates such as PARP and lamin B I.

45-kDa Subunit of DFF is a Substrate for Caspase-3

Inasmuch as activation of DFF by caspase-3 is inhibited by Ac-DEAD-CHO, it is likely that this activation involves the cleavage of one or both of the subunits of DFF. To test this hypothesis, purified DFF was labeled with biotin and incubated the biotinylated DFF with caspase-3. After incubation, the samples were subjected to SDS-PAGE and visualized by chemiluminescence using streptavidin-conjugated peroxidase. Both subunits of DFF were labeled with biotin. Incubation with caspase-3 resulted in the cleavage of the 45-kDa subunit into fragments of molecular masses of 30 kDa and 11 kDa that were separated by SDS-PAGE; the 40-kDa subunit remained intact.

To confirm that DFF-45 is cleaved and activated in vivo in cells undergoing apoptosis, immuno-blot analysis of DFF-45 using extracts from human monocytic U937 cells undergoing apoptosis induced by staurosporine revealed that DFF-45 exists as ~45-kDa precursor in growing cells. After a 2 hr treatment with staurosporine, DFF45 was cleaved into fragments of 30 and 11 kDa. At later time points the 30-kDa fragment was reduced and the 11-kDa increased. The cleavage of DFF-45 into fragments of 30 and 11 kDa has also been observed in other cell types such as HeLa cells and human fibroblast SV589. Similar results were obtained when U937 cells were induced to undergo apoptosis with etoposide. The data suggest that there are multiple caspase-3 cleavage sites in DFF-45. The 30-kDa fragment is an intermediate that is further cleaved to an 11 kDa form. The time of appearance of the 11-kDa fragments correlated well with the fragmentation of chromatin in these U937 cells.

Protein sequencing analysis of DFF-45 and DFF-40 (data from 4 tryptic peptides ranging from 7 to 16 amino acids, 50 amino acids total) revealed that both are previously uncharacterized proteins. A cDNA clone encoding the 45-kDa subunit was isolated based on the protein sequence generated from tryptic digestion of DFF45 followed by Edman degradation. The cDNA contains an open reading frame of 331 amino acids with no obvious homolog with any known protein-s in the data base. The translated product of this cDNA in a rabbit reticulocyte lysate runs at the identical position as purified DFF45 in SDS-PAGE.

To map the caspase-3 cleavage sites in DFF-45, the protein was expressed with a six-histidine tag at the NH2-terminus. The fusion protein migrates at about 45 kDa on SDS-PAGE after purification on a nickel affinity column. Incubation of this fusion protein with caspase-3 resulted in its cleavage into three fragments of 30 kDa, 18 kDa and 11 kDa at the early time point, and the 30 kDa fragment was further cleaved into ~11 kDa fragments with longer incubation. These fragments were separated by SDS-PAGE and electroblotted onto Immobilon Psq for automated Edman degradation. The results revealed that the NH2-terminal residues of the fragments were Gly-2 (30 and 18 kDa), Ser-138 (11 kDa), and Thr-245 (11 kDa) respectively, suggesting that caspase-3 had cleaved between Asp-137 and Ser-138 and between Asp-244 and Thr-245. This generates two different fragments of 11 kDa that could not be separated on SDS-PAGE. The 18 kDa fragment is probably generated as the result of His-tag at the NH2-terminal of the fusion protein, which runs at ~11 kDa if it was from the native DFF-45.

To confirm that these are the principal sites of cleavage, unfractionated samples of digested DFF-45 were subjected to electrospray mass spectrometry. This analysis revealed protein fragments of mass 23,732, 14,833, 12,036 and 11,713 Da. These values corresponded with those calculated for the peptide expected from the results of Edman degradation, namely Ser-138 to Thr-351 (23,736), Gly-2 to Asp-137 (14,836), Ser-138 to Asp-244 (12,039) and Thr-245 to Thr-351 (11,715). The NH2-terminal fragment of DFF-45 runs slowly on SDS-PAGE. The NH2-terminal sequence analysis and the mass spectrometry of the cleavage products revealed that cleavage occurs at the sequence DETD (a.a. 117) and DAVD (a.a. 224). These cleavage sites are consistent with the known cleavage sites for caspase-3 such as DEVD for PARP and DEPD for SREBP-2 (Nicholson et al., 1995; Wang et al., 1995). These data delineate a direct signal transduction pathway during apoptosis: caspase-3 to DFF to DNA fragmentation.

Example 3

The DFF40 Subunit of the DFF Complex Induces Apoptosis

Caspases cleave and activate a heterodimeric protein composed of 40 and 45 kDa subunits designed as DNA Fragmentation Factor (DFF), which mediates the degradation of genomic DNA into nucleosomal fragments (Liu et al., 1997). Both DFF40 and DFF45 are encoded by previously uncharacterized genes whose gene products do not share significant homology with other proteins of known function (Liu et al., 1997). The present Example is directed towards the elucidation of the DFF 40 kDa subunit.

SEQ ID NO:2 shows the sequence of the human DFF40 protein deduced from its cDNA sequence (SEQ ID NO:1) as described herein. This sequence was compared with that of mouse CAD (Enari et al., 1998; Sakahira, et al., 1998). The two proteins are about 71% identical throughout the entire sequence with a noticeable exception of the region between amino acids 41–79 which differs completely between the two proteins. This difference is the result of a change in the reading frame, which is due to a sequencing error in (Enari et al., 1998; Sakahira, et al., 1998). The putative nuclear localization signal previously noticed in the C-terminal of CAD is conserved in DFF40 (Enari et al., 1998; Sakahira, et al., 1998).

To test the ability of recombinant DFF to induce DNA fragmentation, the cDNAs encoding DFF45 and DFF40 were expressed either individually or together by transfection into human embryonic kidney 293 cells as described in Example 1. Extracts from the transfected cells were incubated with hamster liver nuclei in the presence of active caspase-3. Neither DFF40 nor DFF45 expressed alone exhibited a significant increase in DNA fragmentation activity when incubated with nuclei compared with a vector control even though both proteins were expressed as measured by western blot analysis. The antibody against DFF45 also recognized the endogenous protein. However, when both proteins were co-expressed, a dramatic increase in DFF activity was observed. The activity of recombinant DFF was dependent on caspase-3 since no activity was observed when caspase-3 was omitted from the reaction. Thus, these data show that co-expression of both DFF subunits is a requisite for activity.

DFF activity was previously detected and purified in the 100,000 g supernatant, which suggested that latent DFF might be sequestered in the cytosol (Liu et al., 1997). Based on similar observations, Enari et al. proposed that the activation of DNA fragmentation is a result of releasing the cytosolic retention of CAD by ICAD similar to the activation of NF-kB (Enari et al., 1998; Sakahira, et al., 1998). However, unexpectedly, when measured by immunofluorescence staining, the majority of the staining for both DFF40 and DFF45 was observed in nuclei when expressed by transient transfection either alone or together in CV-1 cells as described in Example 1. Such nuclear localization of DFF has been confirmed in several other cell lines, including HeLa cells, SV40-transformed human fibroblast cells, and human embryonic kidney 293 cells. The observation that DFF40 and DFF45 are present in nuclei of non-apoptotic cells suggests that the cytosolic retention model for activation of DFF is likely incorrect. The exclusive presence of DFF in the cytosolic fraction after biochemical fraction is the result of leakage from nuclei during homogenization. Indeed, biochemical fractionation of these transfected cells revealed that DFF40 and DFF-45 exists almost exclusively in the cytosolic fraction. Such nuclear leakage during homogenization has also been previously observed for other nuclear proteins (Paine et al., 1983). DFF45 is therefore like other nuclear substrates of caspase-3 such as poly(ADP-ribose) polymerase and lamins that are cleaved as the result of nuclear translocation of active caspases (Kaufmann, et al., 1993; Lazebnik, et al., 1995).

Latent DFF containing both 40 and 45 kDa subunits becomes activated when DFF45 is cleaved by caspase-3 (Lui et al., 1997). Since co-expression of both DFF40 and DFF45 are required to generate functional recombinant DFF, an *E. coli* expression plasmid that contains both DFF40 and DFF45 cDNAs was engineered with DFF40 tagged with six histidine at its C-terminus as described in Example 1. This double-expression system generated functional DFF, which could be purified through a nickel affinity column. Recombinant DFF was generated using this expression system and purified to homogeneity. Recombinant DFF induced DNA fragmentation when incubated with nuclei in the presence of caspase-3 and an inhibitor of caspase-3 blocked this activity.

In order to determine the mechanism of DFF activation and to identify the active component of DFF after activation, the DFF activation process was reproduced in vitro by activating the pure recombinant DFF through caspase-3 cleavage and purified the active component of DFF by subjecting the activation reaction mixture to a Mono Q column chromatography followed by a Mono S column chromatography. The fractions eluted from these two columns were assayed for active DFF activity by incubating them with hamster liver nuclei without further addition of caspase-3. The fractions that exhibited constitutive DFF activity consisted of only the 40 kDa subunit, indicating that DFF40 is the active form of DFF. The identity of the active DFF as DFF40 was confirmed by western blot analysis using an antibody generated against DFF40 recombinant protein (see Example 1). The fragments of DFF45 generated by caspase-3 cleavage were observed in the column fractions that did not associate with DFF activity. Active DFF purified through the Mono S column induced DNA fragmentation in co-incubated nuclei without a further requirement for caspase-3. The activity was insensitive to the caspase-3 inhibitor. Thereafter, the activated, pure DFF40 was designated as A-DFF40. These data definitively prove that the DFF40 subunit is the active component that induces DNA fragmentation.

Without co-expression of DFF45, DFF40 produced in either mammalian cells or insect cells does not have DFF activity. DFF45, therefore, seems to mediate the correct folding of DFF40 but is not the component of the final functional structure of A-DFF40. Such a function by definition is a molecular chaperone (Hartl et al., 1994). However, unlike the general molecular chaperones like Hsp70 and Hsp60 systems (Hartl et al., 1994), DFF45 remains complexed with DFF40, keeping it from being active until a specific signal is received, in this case, the activation of caspase-3. Such a specific molecular chaperone provides a double safety control to prevent unwanted activation of DFF. First of all, such an arrangement prevents newly synthesized DFF40 from cleaving DNA. Since DFF40 is translocated to nuclei, imbalanced expression of DFF45 and DFF40 could otherwise have a catastrophic effect on the cells by introducing chromatin condensation and fragmentation. Only the DFF40 that is complexed with DFF45 has the potential to generate active DFF. Secondly, by forming a complex with DFF40, DFF45 also prevents DFF40 from activating its DNase activity. In this way, only the DFF heterodimer that is cleaved by caspase-3 will become active. In this sense, DFF45 is also an inhibitor for DFF40, as proposed for ICAD (Enari et al., 1998; Sakahira et al., 1998).

Purified DFF from HeLa cell extracts showed little nuclease activity in the presence of caspase-3 when incubated directly with naked DNA compared to incubation with nuclei (Lui et al., 1997). However, Enari et al. did detect CAD-dependent (DFF40) DNase activity when assayed in a relatively crude system (Enari et al., 1998; Sakahira, et al., 1998). It seemed likely that additional protein(s) were required to generate a nuclease activity that cleaved chromatin DNA at the inter-nucleosomal linker regions during apoptosis. Therefore an assay was set up to search for additional protein factors from HeLa cell high salt nuclear extracts that may work together with activated DFF to generate high level DNase activity that directly cleaves purified plasmid DNA. The inventors identified and purified such a protein from HeLa cell nuclear extracts and protein sequencing analysis revealed that it was high mobility group (HMG) protein-2. Thus other chromatin associated proteins, such as core histones, histone H1, and other HMG proteins were tested for stimulation of DFF-dependent DNase activity. Histone H1 and HMG-1 stimulated the DNase activity of DFF40 when incubated with purified plasmid DNA while the core histones and bovine serum albumin (BSA) showed little effects. To further demonstrate the stimulatory effects of chromatin associated proteins, the DNase activity of DFF40 was assayed with increasing concentrations of A-DFF40 in the presence and absence of histone H1. A-DFF40 manifested its intrinsic DNase activity only when high concentrations of A-DFF40 were used. Little DNase activity was detected at lower concentrations unless histone H1 was present. The stimulatory effect of histone H1 was more than 10-fold. The finding that abundant chromatin-associated proteins, such as HMG-1, HMG-2, HMG-14 and histone H1 can markedly stimulate the intrinsic DNase activity of DFF40 suggests that rather than passively cleaving chromatin DNA at the linker region because of its greater accessibility to nuclease, DFF-dependent DNase is targeted directly to the nucleosomal linker region of chromatin where the HMG proteins and histone H1 are known to be located (Jackson, 1979; Peters, 1979; Schroter and Bode, 1982). In addition, since histone H1 and HMGs also are believed to be involved in organizing high order chromatin structure (Jackson, 1979; Peters, 1979; Schroter and Bode, 1982), these proteins may also facilitate A-DFF40 (CAD) DNase to disassemble these high order chromatin structures. Such a model would provide a more efficient way to disassemble complex chromatin DNA into nucleosomes as compared to disassembly by random cleavage of DNA. The molecular mechanism by which these chromatin-associated proteins stimulate A-DFF40 DNase activity should be an interesting topic for future study.

Chromatin condensation is one of the morphological hallmarks of apoptosis (Kerr, et al., 1972; Wyllie, et al., 1980; Wyllie, et al., 1980; Wyllie, et al., 1984). The molecular mechanism for apoptosis-associated chromatin condensation, however, is unknown. Unexpectedly, when latent DFF plus caspase-3, or A-DFF40 was incubated with isolated nuclei, chromatin DNA became condensed into several small bright granules, a typical nuclear morphology observed when cells are undergoing apoptosis (Wyllie, et al., 1980; Wyllie, et al., 1980; Wyllie, et al., 1984). The control nuclei, on the other hand, demonstrated uniform DNA staining throughout the nuclear interior. Addition of caspase-3, or latent DFF alone had no effect on the DNA staining patterns of these nuclei. A general caspase inhibitor, z-VAD-fmk, had no effect on DNA condensation when A-DFF40 was used, indicating that DFF is different from AIF, a z-VAD sensitive mitochondrial protein that triggers apoptosis in nuclei (Zamzami et al., 1996).

The finding that A-DFF40 mediates chromatin condensation puts DFF in a central position responsible for the observed terminal nuclear changes during apoptosis. It is possible that DFF triggers chromatin condensation by cleaving chromatin DNA. However, it has been reported that treatment of isolated nuclei with micrococcal nuclease induces nucleosomal DNA fragmentation but nevertheless has no effect on chromatin condensation (Sun et al., 1994). It is interesting to note that cleavage of DNA at the nucleosomal linker region by micrococcal nuclease is blocked, not facilitated, by the presence of histone H1 (Roche et a., 1985). It is also possible that A-DFF40 activates an independent pathway leading to chromatin condensation. All these become testable hypotheses now with the availability of pure recombinant DFF.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alnemri et al., *Cell* 87, 171, 1996.
Arcone et al., *Nuc. Acids Res.* 16(8):3195–3207, 1988.
Baichwal and Sugden, In: *Gene Transfer*, Kucherlapati R, ed., New York, Plenum Press, pp. 117–148, 1986.
Barany and Merrifield, The Peptides, Gross and Meienhofer, eds., Academic Press, New York, pp. 1–284, 1979.
Bartlett et al., *Proc. Natl. Acad. Sci. USA*, 93:8852–8857, 1996.
Batterson and Roizman, *J. Virol.*, 46:371–377, 1983.
Bellon et al., *de Ses Filiales*, 190(1):109–142, 1996.
Bellus, *J. Macromol. Sci. Pure Appl. Chem*, A31(1): 1355–1376, 1994.
Benvenisty and Neshif, *Proc. Nat. Acad. Sci. USA*, 83:9551–9555, 1986.
Berns and Bohenzky, *Adv. Virus Res.*, 32:243–307, 1987.
Berns and Giraud, *Curr. Top. Microbiol. Immunol.*, 218:1–23, 1996.
Bertran, et al., *J Virol.*, 70(10):6759–6766, 1996.
Brinster et al., *Proc. Nat'l Acad. Sci. USA*, 82: 4438–4442, 1985.
Campbell et al., *J. Mol. Biol.*, 180:1–19, 1984.
Capaldi et al., *Biochem. Biophys. Res. Comm.*, 76:425, 1977.
Casicola-Rosen, et al, *J. Exp. Med*, 183:1957–1964, 1996.
Chen and Okayama, *Mol. Cell Biol.*, 7:2745–2752, 1987.
Chinnaiyan et al., *J. Biol. Chem*, 271:4573–4576, 1996.
Coffin, In: *Virology*, ed., New York: Raven Press, pp. 1437–1500, 1990.
Cook et al., *Cell*, 62:671–680, 1990.
Cook et al., "In vitro splicing of the ribosomal RNA precursor of Tetrahymena: involvement of a guanosine nucleotide in the excision of the intervening sequence," *Cell*, 27:487–496, 1981.
Couch et al., *Am. Rev. Resp. Dis.*, 88:394–403, 1963.
Culver et al., *Science*, 256:1550–1552, 1992.
Darmon et al., *J. Biol. Chem.*, 271:21709–21712, 1996.
Datta et al., *Blood*, 88:1936–1943, 1996.
Datta et al., *L Biol. Chem.*, 272:1965–1969, 1997.
Davey et al., EPO No. 329 822
DeLuca et al., *J. Virol.*, 56:558–570, 1985.
Dubensky et al., *Proc. Nat. Acad. Sci. USA*, 81:7529–7533, 1984.
Dubrez et al., *EMBO, J.*, 15:5504–5512, 1996.
Elroy-Stein et al., *Proc. Nat'l Acad. Sci. USA*, 1989.
Elshami et al., *Gene Therapy*, 7(2):141–148, 1996.
Enari et al., *Nature*, 391:43, 1998.
Enari, et al. *Nature* 380:723–726, 1996.
EPO No. 320 308
Erhardt and Cooper, *J. Biol. Chem.*, 271:17601–17604, 1996.
Faleiro et al., *EMBO J.*, 16:2271, 1997.
Fechheimer et al., *Proc. Natl. Acad. Sci. USA*, 84:8463–8467, 1987.
Ferkol et al., *FASEB J.*, 7:1081–1091, 1993.

Fernandes-Alnemri et al., *J. Biol. Chem.*, 269:30761–30764, 1994.
Fodor et al., *Science*, 251:767–773, 1991
Forster and Symons, *Cell*, 49:211–220, 1987.
Fraley et al., *Proc. Natl. Acad. Sci. USA*, 76:3348–3352, 1979.
Freifelder, *Physical Biochemistry—2d Ed.*, W. H. Freeman & Co., 1982.
French et al., *Circulation*, 90(5):2414–2424, 1994.
Freshner, "Animal Cell Culture: a Practical Approach," Second Edition, Oxford/N.Y., IRL Press, Oxford University Press, 1992.
GB Application No. 2 202 328
Gefter et al., *Somatic Cell Genet.*, 3: 231–236, 1977
Gerlach et al., *Nature (London)*, 328:802–805, 1987.
Ghosh-Choudhury et al., *EMBO J.*, pp. 1733–1739, 1987.
Ghosh and Bachhawat, (Wu G, Wu C ed.), New York: Marcel Dekker, pp. 87–104, 1991.
Gingeras et al., PCT Application WO 88/10315
Gingeras et al., WO 88/10315
Ginsberg et al., *Proceedings of the National Academy of Sciences of the United States of America*, 88(5) 1651–1655, 1991.
Glorioso et al., *Ann. Rev. Microbiol*, 49:675–710, 1995.
Goding, In: *Monoclonal Antibodies: Principles and Practice*, 2d ed., Academic Press, Orlando, Fla., pp. 60–61 and 71–74, 1986.
Goldberg et al., *Nat. Genet.*, 13(4):442–449, 1996.
Gomez-Foix et al., *J. Biol. Chem.*, 267:25129–25134, 1992.
Gopal, *Mol. Cell Biol.*, 5:1188–1190, 1985.
Gossen and Bujard, *Proc. Natl. Acad. Sci. USA*, 89:5547–5551, 1992.
Gossen et al., *Science*, 268:1766–1769, 1995.
Graham and Prevec, *Biotechnology*, 20:363–390, 1992.
Graham and Prevec, In: *Methods in Molecular Biology: Gene Transfer and Expression Protocols* 7, E. J. Murray (ed.), Clifton, N.J., Humana Press, pp. 205–225, 1991.
Graham and Van Der Eb, *Virology*, 52:456–467, 1973.
Graham et al., *J. Gen. Virol.*, 36:59–72, 1977.
Grunhaus and Horwitz, *Seminar in Virology*, 3:237–252, 1992.
Hacia et al., *Nature Genetics*, 14:441–447, 1996.
Harland and Weintraub, *J. Cell Biol.*, 101:1094–1099, 1985.
Harlow et al., Antibodies: A Laboratory Manual, Cold Spring Harbor, N.Y., 1988
Hartl et al., *TIBS*, 19, 20, 1994.
Hasegawa et al., *Cancer Res.*, 56:1713–1718, 1996.
Hersdorffer et al., *DNA Cell Biol.*, 9:713–723, 1990.
Herz and Gerard, *Proc. Nat'l Acad. Sci. USA*, 90:2812–2816, 1993.
Holland et al., *Virology*, 101:10–18, 1980.
Honess and Roizman, *J. Virol.*, 14:8–19, 1974.
Honess and Roizman, *J. Virol.*, 16:1308–1326, 1975.
Innis et al., *PCR Protocols*, Academic Press, Inc., San Diego Calif., 1990.
Jackson et al., *Biochemistry*, 18:3739, 1979.
Jacobson et al., *J. Cell. Biol.*, 133:1041–1051, 1996.
Jarlais, S. B. Horvitz, *J. Cell Biol.* 97, 1240 (1983).
Johnson et al., Peptide Turn Mimetics" IN: *Biotechnology And Pharmacy*, Pozzuto et al., eds., Chapman and Hall, New York, 1993.
Joki et al., *Human Gene Ther.*, 6:1507–1513, 1995.
Jones and Shenk, *Cell*, 13:181–188, 1978.
Jones and Shenk, *Cell*, 13:181–188, 1978.
Joyce, *Nature*, 338:217–244, 1989.
Kageyama et al., *J. Biol. Chem.*, 262(5):2345–2351, 1987.
Kaneda et al., *Science*, 243:375–378, 1989.

Karlsson et al., *EMBO J.*, 5:2377–2385, 1986.
Kato et al, *J. Biol. Chem.*, 266:3361–3364, 1991.
Kaufmann, et al. *Cancer Res.* 53, 3976–3985, 1993.
Kearns et al., *Gene Ther.*, 3:748–755, 1996.
Kerr et al., *Br. J. Cancer*, 26:239, 1972.
Khokhlatchev et al., *J. Biol. Chem.* 272:11057, 1997.
Kim and Cook, *Proc. Natl. Acad. Sci. USA*, 84:8788–8792, 1987.
Klein et al., *Nature*, 327:70–73, 1987.
Kohler and Milstein, *Eur. J. Immunol.* 6:511–519, 1976.
Kohler and Milstein, *Nature*, 256:495–497, 1975.
Kotin and Berns, *Virol.*, 170:460–467, 1989.
Kotin et al., *Genomics*, 10:831–834, 1991.
Kotin et al., *Proc. Natl. Acad. Sci. USA*, 87:2211–2215, 1990.
Kuida et al., *Nature*, 384:368–372, 1996.
Kwoh et al., *Proc. Nat. Acad. Sci. USA*, 86: 1173, 1989.
Kyte and Doolittle, *J. Mol. Biol.*, 157(1):105–132, 1982.
Lazebnik et al., *Proc. Natl. Acad. Sci.*, 92:9042, 1995.
Le Gal La Salle et al., *Science*, 259:988–990, 1993.
Levrero et al., *Gene*, 101:195–202, 1991.
Liu et al, *Cell*, 86:147, 1996.
Liu et al., *Cell*, 86:147–157, 1996b.
Liu et al., *Cell*, 89:175, 1997.
Liu et al., *J. Biol. Chem.*, 271:13371–13376, 1996a.
Luo and Sawadogo, *Mol. Cell Biol.*, 16(4):1367, 1996.
Macejak and Sarnow, *Nature*, 353:90–94, 1991.
Manipulating the Mouse Embryo: A Laboratory Manual, 2nd ed., Hogan et al., eds., Cold Spring Harbor Laboratory Press, 1994.
Mann et al., *Cell*, 33:153–159, 1983.
Markowitz et al., *J. Virol.*, 62:1120–1124, 1988.
Martin et al., *EMBO J.*, 15:2407–2416, 1996.
Martins et al., *J. Biol. Chem.*, 272:7421, 1997.
Merrifield, *Science*, 232: 341–347, 1986.
Michel and Westhof, *J. Mol. Biol.*, 216:585–610, 1990.
Miller et al., WO 89/06700
Mizukami et al., *Virology*, 217:124–130, 1996.
Mulligan, "The Basic Science of Gene Therapy," *Science*, 260:926–932, 1993.
Myers, EPO 0273085
Na et al., *J. Biol. Clam.*, 271:11209–11213, 1996.
Nicholson and Thornberry, *TIBS* 257:299, 1997.
Nicholson et al., *Nature*, 376:3743, 1995.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochim. Biophys. Acta*, 721:185–190, 1982.
Nicolau et al., *Methods Enzymol.*, 149:157–176, 1987.
Ogawa, *Neuropathologica*, 77(3):244–253, 1989.
Ohara et al., *Proc. Nat'l Acad. Sci. USA*, 86: 5673–5677, 1989.
Olivierio et al., *EMBO J.*, 6(7):1905–1912, 1987.
Ostrove et al., *Virology*, 113:532–533, 1981.
Paine, et al, *Cancer Res.*, 53:3976, 1983.
Paskind et al., *Virology*, 67:242–248, 1975.
PCT Application No. PCT/US87/00880
PCT Application No. PCT/US89/01025
Pease et al., *Proc. Natl. Acad. Sci. USA*, 91:5022–5026, 1994.
Pelletier and Sonenberg, *Nature*, 334:320–325, 1988.
Perales et al., *Proc. Natl. Acad. Sci.*, 91:4086–4090, 1994.
Peters et al., *J. Biol. Chem.*, 254:3358, 1979.
Pignon et al., *Hum. Mutat.*, 3: 126–132, 1994.
Pinkel et al., U.S. Pat. No. 5,665,549
Pinkel et al., U.S. Pat. No, 5,672,344

Poli and Cortese, *Proc. Natl. Acad. Sci. USA*, 86:8202–8206, 1989.
Ponnazhagan et al., *Hum. Gene Ther.*, 8:275–284, 1997a.
Ponnazhagan et al., *J. Gen. Virol.*, 77:1111–1122, 1996.
Post et al., *Cell*, 24:555–565, 1981.
Potter et al., *Proc. Nat'l Acad. Sci. USA*, 81:7161–7165, 1984.
Prowse and Baumann, *Mol Cell Biol*, 8(1):42–51, 1988.
Racher et al., *Biotechnology Techniques*, 9:169–174, 1995.
Radler et al., *Science*, 275:810–814, 1997.
Ragot et al., *Nature*, 361:647–650, 1993.
Reinhold-Hurek and Shub, *Nature*, 357:173–176, 1992.
Renan, *Radiother. Oncol.*, 19:197–218, 1990.
Rich et al., *Hum. Gene Ther.*, 4:461–476, 1993.
Ridgeway, In: *Vectors: A survey of molecular cloning vectors and their uses*, Rodriguez R L, Denhardt D T, ed., Stoneham:Butterworth, pp.467–492, 1988.
Rippe et al., *Mol. Cell Biol.*, 10:689–695, 1990.
Roche et al, *Nucleic Acids Res.*, 13:2843, 1985.
Roizman and Sears, In *Fields' Virology*, 3rd Edition, eds. Fields et al. (Raven Press, New York, N.Y.), pp. 2231–2295, 1995.
Ron et al., *Mol. Cell Biol.*, 2887–2895, 1991.
Rosenfeld et al., *Cell*, 68:143–155, 1992.
Rosenfeld et al., *Science*, 252:431–434, 1991.
Roux et al., *Proc. Natl Acad. Sci. USA*, 86:9079–9083, 1989.
Sakahira et al., *Nature*, 391:96, 1998.
Sambrook et al., Mol. Cloning A Lab. Manual, 2rid ed, Cold Spring Harbor Lab Press.
Samulski et al, *EMBO J.*, 10:3941–3950, 1991.
Sarver et al., *Science*, 247:1222–1225, 1990.
Scanlon et al., *Proc Natl Acad Sci USA*, 88:10591–10595, 1991.
Schlegel et al., *J. Biol. Chem.*, 271:1841, 1996.
Schroter and Bode, *Eur. J. Biochem.*, 127:429, 1982.
Shiraishi et al., *Transplant Internationl*, 1–0(3):202–206, 1997.
Shoemaker et al., *Nature Genetics* 14:450–456, 1996.
Smith and Moss, *Gene*, 25:21–28, 1983.
Song et al., *EMBO, J.*, 15:3238–3246, 1996.
Song et al., *Science*, 275:536–540, 1997.
Srivastava et al., *J. Virol.*, 45:555–564, 1983.
Stewart and Young, Solid Phase Peptide Synthesis, 2d. ed., Pierce Chemaical Co., 1984.
Stratford-Perricaudet and Perricaudet, In: *Human Gene Transfer*, Eds, O. Cohen-Haguenauer and M. Boiron, Editions John Libbey Eurotext, France, p. 51–61, 1991.
Stratford-Perricaudet et al., *Hum. Gene Ther.*, 1:241–256, 1990.
Sun et al, *J. Exp. Med.*, 179:559, 1994.
Takahashi et al., *Oncogene*, 14:2741, 1997.
Tam et al., *J. Am. Chem. Soc.*, 105:6442, 1983.
Temin, In: *Gene Transfer*, Kucherlapati (ed.), New York: Plenum Press, pp. 149–188, 1986.
Tewari et al., *Cell*, 81:801, 1995.
Top et al., *J. Infect. Dis.*, 124:155–160, 1971.
Tur-Kaspa et al., *Mol. Cell Biol.*, 6:716–718, 1986.
U.S. Pat. No. 4,196,265
U.S. Pat. No. 4,554,101
U.S. Pat. No. 4,683,195
U.S. Pat. No. 4,683,202
U.S. Pat. No. 4,800,159
U.S. Pat. No. 4,873,191
U.S. Pat. No. 4,883,750
U.S. Pat. No. 5,252,479
U.S. Pat. No. 5,279,721
U.S. Pat. No. 5,633,365

Varmus et al., *Cell*, 25:23–36, 1981.
Vaux, *Cell*, 90:389, 1997.
Wagner et al., *Proc. Natl. Acad. Sci.*, 87(9):3410–3414, 1990.
Walker et al., *Proc. Natl. Acad. Sci. USA*, 89:392–396, 1992.
Walther and Stein, *J. Mol. Med.*, 74:379–392, 1996.
Wang et al., *EMBO J.*, 15:1012–1020, 1996.
Wang et al., *Gene & Dev.*, 9:509–520, 1995.
Wang et al., *J. Biol. Chem.*, 268:14497–14504, 1993.
Wang et al., *J. Biol. Chem.*, 270:18044–18050, 1995.
Wang et al., *J. Cell Biol.*, 129:1103, 1995.
Watt et al., Proc. Natl Acad. Sci., 83(2):3166–3170, 1986.
Werthman et al.,*Journal of Urology*, 155(2):753–756, 1996.
White, *Genes & Dev.*, 10:1–15, 1996.
Wilson et al., *Mol. Cell. Biol.*, 6181–6191, 1990.
WO 90/07641
Wong et al., *Gene*, 10:87–94, 1980.
Wu and Wu, *Adv. Drug Delivery Rev.*, 12:159–167, 1993.
Wu and Wu, *Biochem.*, 27:887–892, 1988.
Wu and Wu, *J. Biol. Chem.*, 262:4429–4432, 1987.
Wu et al., *Genomics*, 4:560, 1989
Wyllie et al, *Int. Rev. Cytol.*, 68:251, 1980.
Wyllie et al, *J. Pathol*, 142:66, 1984.
Wyllie, *Curr. Opin. in Can. and Dev.*, 5:97–104, 1995.
Wyllie, *Nature*, 284:555–556, 1980.
Xue et al., *Genes & Dev.*, 10:1073–1083, 1996.
Yang et al., *Proc. Natl. Acad. Sci USA*, 87:9568–9572, 1990.
Yokoyama et al., *Cell*, 75:187, 1993.
Yuan et al., *Cell*, 75: 641–652, 1993.
Zamzami et al., *J. Exp. Med.*, 183:1523, 1996.
Zechner et al., *Mol. Cell. Biol.*, 2394–2401, 1988.
Zou et al, *Cell*, 90:405, 1997.

What is claimed is:

1. An isolated polypeptide comprising a DNA fragmentation factor, wherein the DNA fragmentation factor comprises SEQ ID NO:2.

2. An isolated polypeptide comprising 23 contiguous amino acids of SEQ ID NO:2.

3. The polypeptide of claim 2, wherein the polypeptide comprises 30 contiguous amino acids of SEQ ID NO:2.

4. The polypeptide of claim 3, wherein the polypeptide comprises 50 contiguous amino acids of SEQ ID NO:2.

5. The polypeptide of claim 4, wherein the polypeptide comprises 100 contiguous amino acids of SEQ ID NO:2.

* * * * *

SEQUENCE LISTING

<160> NUMBER OF SEQ ID NOS: 21

<210> SEQ ID NO 1
<211> LENGTH: 2839
<212> TYPE: DNA
<213> ORGANISM: Homo sapiens

<400> SEQUENCE: 1

```
ggcacccggc ctgtgccagc ttgcagagct caccaggtgc agaccctgc  ggccagggcg      60 aggacggatc tgagcagctg ggcagcaggt gccaccgcct gtgggaccca gagggcttga     120
ggacatctgc aatgctccag aagcccaaga gcgtgaagct gcgggccctg cgcagcccga     180
ggaagttcgg cgtggctggc cggagctgcc aggaggtgct gcgcaagggc tgtctccgct     240
tccagctccc tgagcgcggt tcccggctgt gcctgtacga ggatggcacg gagctgacgg     300
aagattactt ccccagtgtt cccgacaacg ccgagctggt gctgctcacc ttgggccagg     360
cctggcaggg ctatgtgagc gacatcaggc gcttcctcag tgcatttcac gagccacagg     420
tggggctcat ccaggccgcc cagcagctgc tgtgtgatga gcaggcccca cagaggcaga     480
ggctgctggc tgacctcctg cacaacgtca gccagaacat cgcggccgag acccgggctg     540
aggacccgcc gtggtttgaa ggcttggagt cccgatttca gagcaagtct ggctatctga     600
gatacagctg tgagagccgg atccggagtt acctgaggga ggtgagctcc taccctcca     660 cagtgggtgc ggaggctcag gaggaattcc tgcgggtcct cggctccatg tgccagaggc     720
tccggtccat gcagtacaat ggcagctact tcgacagagg agccaagggc ggcagccgcc     780
tctgcacacc ggaaggctgg ttctcctgcc agggtccctt tgacatggac agctgcttat     840
caagacactc catcaacccc tacagtaaca gggagagcag gatcctcttc agcacctgga     900
acctggatca cataatagaa aagaaacgca ccatcattcc tacactggtg gaagcaatta     960
aggaacaaga tggaagagaa gtggactggg agtattttta tggcctgctt tttacctcag    1020
agaacctaaa actagtgcac attgtctgcc ataagaaaac cacccacaag ctcaactgtg    1080
acccgagcag aatctacaaa ccccagacaa ggttgaagcg gaagcagcct gtgcggaaac    1140
gccagtgaca cgtacacacc acgtcctggt ctttgtttga ggcctgacgt gggcatcatt    1200
ttaacaggtg cctttttgt tttttgttt ttcgttttt tggtcactcc agtagctcct       1260
ggaaaaaacc ttaaaaatg tttcctccaa atctgatttc attacatttc tgaattgttg    1320 ggttttttt tgttgttttg ttttgttttg tagatggagt ttcactttg ttgcccaggc      1380
```

-continued

```
tggagtgtag tggcgcgatc tcggctcagc ctcccgagta gctgggatta caggcatgtg   1440
ccaccacgcc cggctaatgt ttgtattttt agtagagacg gggtttcacc atgttggtca   1500
ggctggtctc aaactcctga cctcaggtga tccgcccacc tcagcctccc aaagtgctgg   1560
gatgacaggt gtgagccact gcgcccagcc tgaatcattt cttataccct ctgacagccc   1620
aacttccaga ggacagctct ggggtactcg ttggatgtct gtgagtacct ggtcatacgg   1680
gtcagtaggg ataagaattg tctctgggct gaggaattct tctgttctct ggtttcacca   1740
gcgttgggtt tgctcatgta atgtggtcac catactcaaa tggtgtcatg gctgaagttg   1800
gccaccttgc ttgagggaca agttgtttat gtatcagctc tctgctgggt ctccctttcc   1860
atggcaaatg ggcagctcca tcctcttgat cttctaaatg cccaaaagag gtgtcatgct   1920 ttggggtac gatgtttata ctccgtaaag aacatacaag gacattcact gctgattttt    1980 tttttttgttt gtttgagaca gggtctcact ctgtcgctca ggctggagtg cagtgatgca   2040
atcttggctc actgcaacct ccgcctctca ggttcaagtg ttctcctgc ctcagcctcc    2100 caagtagctg ggattacagg cacctaccac cagggccagc taattttttgt atgtttagta  2160 gtaacggggt tcaccatgt tggccaggct gttctcgaac tcctgacctc aggtgatctg    2220
cccgcctcgg tctcccaaag tgctgggatt acaggcatga gccactgcac ctgacctgct   2280
gaattgttta taatggcaag aaataggaaa ccccccaatg tctgttgaac agctatcacg   2340
ttgaaccacg tgaaactgct gttttctagg ccaaaaatgg tgagcgatca tttatttcat   2400
gattcaacct gatacattta catagtgcaa aactgtgtca cagtttcagg cttttatgag   2460
gaaagcgttt ctgtgtagaa actggaagct gttcagggca tcggcagctg aaccctgctc   2520
cgttggtcag cgttactatc atctcggatc atatggagct catgtcagcc gtgtgggtgg   2580
cgggtgcaca gagacggtct ggaaggaaac acgcggatct gaacagcagt aatcctgggg   2640
gatacggggg ttgggctaga ttacagaggg ctcattttct acgtcatgta ttttatgata   2700
cttgaatttt ttgaaatggg catttatttt ataacatgtt aaaatgtact ttttaaatta   2760
agtcattttg taatatttga atttttacat ttgttgtaca atcaggaaaa gcaataaaga   2820
tttttcaaaa ataaaaaaa                                                2839
```

<210> SEQ ID NO 2
<211> LENGTH: 338
<212> TYPE: PRT
<213> ORGANISM: Homo sapiens

<400> SEQUENCE: 2

```
Met Leu Gln Lys Pro Lys Ser Val Lys Leu Arg Ala Leu Arg Ser Pro
  1               5                  10                  15

Arg Lys Phe Gly Val Ala Gly Arg Ser Cys Gln Glu Val Leu Arg Lys
             20                  25                  30

Gly Cys Leu Arg Phe Gln Leu Pro Glu Arg Gly Ser Arg Leu Cys Leu
         35                  40                  45

Tyr Glu Asp Gly Thr Glu Leu Thr Glu Asp Tyr Phe Pro Ser Val Pro
     50                  55                  60

Asp Asn Ala Glu Leu Val Leu Leu Thr Leu Gly Gln Ala Trp Gln Gly
 65                  70                  75                  80

Tyr Val Ser Asp Ile Arg Arg Phe Leu Ser Ala Phe His Glu Pro Gln
                 85                  90                  95

Val Gly Leu Ile Gln Ala Ala Gln Gln Leu Leu Cys Asp Glu Gln Ala
            100                 105                 110
```

```
Pro Gln Arg Gln Arg Leu Leu Ala Asp Leu Leu His Asn Val Ser Gln
            115                 120                 125

Asn Ile Ala Ala Glu Thr Arg Ala Glu Asp Pro Pro Trp Phe Glu Gly
        130                 135                 140

Leu Glu Ser Arg Phe Gln Ser Lys Ser Gly Tyr Leu Arg Tyr Ser Cys
145                 150                 155                 160

Glu Ser Arg Ile Arg Ser Tyr Leu Arg Glu Val Ser Ser Tyr Pro Ser
                165                 170                 175

Thr Val Gly Ala Glu Ala Gln Glu Glu Phe Leu Arg Val Leu Gly Ser
            180                 185                 190

Met Cys Gln Arg Leu Arg Ser Met Gln Tyr Asn Gly Ser Tyr Phe Asp
        195                 200                 205

Arg Gly Ala Lys Gly Gly Ser Arg Leu Cys Thr Pro Glu Gly Trp Phe
    210                 215                 220

Ser Cys Gln Gly Pro Phe Asp Met Asp Ser Cys Leu Ser Arg His Ser
225                 230                 235                 240

Ile Asn Pro Tyr Ser Asn Arg Glu Ser Arg Ile Leu Phe Ser Thr Trp
                245                 250                 255

Asn Leu Asp His Ile Ile Glu Lys Lys Arg Thr Ile Ile Pro Thr Leu
            260                 265                 270

Val Glu Ala Ile Lys Glu Gln Asp Gly Arg Glu Val Asp Trp Glu Tyr
        275                 280                 285

Phe Tyr Gly Leu Leu Phe Thr Ser Glu Asn Leu Lys Leu Val His Ile
    290                 295                 300

Val Cys His Lys Lys Thr Thr His Lys Leu Asn Cys Asp Pro Ser Arg
305                 310                 315                 320

Ile Tyr Lys Pro Gln Thr Arg Leu Lys Arg Lys Gln Pro Val Arg Lys
                325                 330                 335

Arg Gln

<210> SEQ ID NO 3
<211> LENGTH: 1689
<212> TYPE: DNA
<213> ORGANISM: Homo sapiens
<220> FEATURE:
<221> NAME/KEY: CDS
<222> LOCATION: (113)..(1105)

<400> SEQUENCE: 3
gcgtcgaccg aactacatct cccggcaggc tgcggaaggg ggtcgagtag aaggaccgcc      60
gctccggcct cccgcgactt ctcgaaggtg ggcaggtccc accttgtgga gg atg gag    118
                                                         Met Glu
                                                           1 gtg acc ggg gac gcc ggg gta cca gaa tct ggc gag atc cgg act cta      166
Val Thr Gly Asp Ala Gly Val Pro Glu Ser Gly Glu Ile Arg Thr Leu
        5                   10                  15 aag ccg tgt ctg ctg cgc cgc aac tac agc cgc gaa cag cac ggc gtg      214
Lys Pro Cys Leu Leu Arg Arg Asn Tyr Ser Arg Glu Gln His Gly Val
    20                  25                  30 gcc gcc tcc tgc ctc gaa gac ctg agg agc aag gcc tgt gac att ctg      262
Ala Ala Ser Cys Leu Glu Asp Leu Arg Ser Lys Ala Cys Asp Ile Leu
35                  40                  45                  50 gcc att gat aag tcc ctg aca cca gtc acc ctt gtc ctg gca gag gat      310
Ala Ile Asp Lys Ser Leu Thr Pro Val Thr Leu Val Leu Ala Glu Asp
                55                  60                  65 ggc acc ata gtg gat gat gac gat tac ttt ctg tgt cta cct tcc aat      358
Gly Thr Ile Val Asp Asp Asp Asp Tyr Phe Leu Cys Leu Pro Ser Asn
```

-continued

```
                     70                  75                  80
act aag ttt gtg gca ttg gct agt aat gag aaa tgg gca tac aac aat        406
Thr Lys Phe Val Ala Leu Ala Ser Asn Glu Lys Trp Ala Tyr Asn Asn
             85                  90                  95 tca gat gga ggt aca gct tgg att tcc caa gag tcc ttt gat gta gat        454
Ser Asp Gly Gly Thr Ala Trp Ile Ser Gln Glu Ser Phe Asp Val Asp
    100                 105                 110 gaa aca gac agc ggg gca ggg ttg aag tgg aag aat gtg gcc agg gag        502
Glu Thr Asp Ser Gly Ala Gly Leu Lys Trp Lys Asn Val Ala Arg Glu
115                 120                 125                 130 ctg aaa gaa gat ctg tcc agc atc atc ctc cta tca gag gag gac ctc        550
Leu Lys Glu Asp Leu Ser Ser Ile Ile Leu Leu Ser Glu Glu Asp Leu
                135                 140                 145 cag atg ctt gtt gac gct ccc tgc tca gac ctg gct cag gaa cta cgt        598
Gln Met Leu Val Asp Ala Pro Cys Ser Asp Leu Ala Gln Glu Leu Arg
        150                 155                 160 cag agt tgt gcc acc gtc cag cgg ctg cag cac aca ctc caa cag gtg        646
Gln Ser Cys Ala Thr Val Gln Arg Leu Gln His Thr Leu Gln Gln Val
            165                 170                 175 ctt gac caa aga gag gaa gtg cgt cag tcc aag cag ctc ctg cag ctg        694
Leu Asp Gln Arg Glu Glu Val Arg Gln Ser Lys Gln Leu Leu Gln Leu
    180                 185                 190 tac ctc cag gct ttg gag aaa gag ggc agc ctc ttg tca aag cag gaa        742
Tyr Leu Gln Ala Leu Glu Lys Glu Gly Ser Leu Leu Ser Lys Gln Glu
195                 200                 205                 210 gag tcc aaa gct gcc ttt ggt gag gag gtg gat gca gta gac acg ggt        790
Glu Ser Lys Ala Ala Phe Gly Glu Glu Val Asp Ala Val Asp Thr Gly
                215                 220                 225 atg agc aga gag acc tcc tcg gac gtt gcg ctg gcg agc cac atc ctt        838
Met Ser Arg Glu Thr Ser Ser Asp Val Ala Leu Ala Ser His Ile Leu
        230                 235                 240 act gca ctg agg gag aag cag gct cca gag ctg agc tta tct agt cag        886
Thr Ala Leu Arg Glu Lys Gln Ala Pro Glu Leu Ser Leu Ser Ser Gln
            245                 250                 255 gat ttg gag ttg gtt acc aag gaa gac ccc aaa gca ctg gct gtt gcc        934
Asp Leu Glu Leu Val Thr Lys Glu Asp Pro Lys Ala Leu Ala Val Ala
    260                 265                 270 ttg aac tgg gac ata aag aag acg gag act gtt cag gag gcc tgt gag        982
Leu Asn Trp Asp Ile Lys Lys Thr Glu Thr Val Gln Glu Ala Cys Glu
275                 280                 285                 290 cgg gag ctc gcc ctg cgc ctg cag cag acg cag agc ttg cat tct ctc       1030
Arg Glu Leu Ala Leu Arg Leu Gln Gln Thr Gln Ser Leu His Ser Leu
                295                 300                 305 cgg agc atc tca gca agc aag gcc tca cca cct ggt gac ctg cag aat       1078
Arg Ser Ile Ser Ala Ser Lys Ala Ser Pro Pro Gly Asp Leu Gln Asn
        310                 315                 320 cct aag cga gcc aga cag gat ccc aca tagcagcagc gggaagtgtg             1125
Pro Lys Arg Ala Arg Gln Asp Pro Thr
            325                 330 ccaaggaagc tctgtggcgt tgtgttattg gtagacaccc tcagcctcat catttgacta     1185
cctatgtact actctacccc ctgccttaga gcaccttcca gagaagctat tccaggtctc     1245
aacatacgcc gttccaccaa ttttttttt agccccacca gcttcaggac ttctgccaat      1305
tttgaatgat atagctgcac caacaatatc ccgcctcctc taattacata tgatgttctc     1365
tgttcaaaag taattggcag tgattggcca ggcgcagtgg ctcacgcctg taatcccagc     1425
actgggaggc cgaggggggc ggatcgtgaa gtcaggagat cgagaccatc ctggctaaca     1485
tggtgaaacc ctgtctctac taaaaataca aaaaaaatta gccagccatg gtggcgggcg     1545
```

```
cctgtaatcc cagctacttg ggaggctgag gcaggagaat ggcatgaacc tgggaggcag    1605
agcttgcagt gagctgagat tgcgccactg cactccagcc tgggcaacag agcgagactc    1665
cgtctcaaaa aaaaaaaaaa aaaa                                           1689
```

<210> SEQ ID NO 4
<211> LENGTH: 331
<212> TYPE: PRT
<213> ORGANISM: Homo sapiens

<400> SEQUENCE: 4

```
Met Glu Val Thr Gly Asp Ala Gly Val Pro Glu Ser Gly Glu Ile Arg
 1               5                  10                  15

Thr Leu Lys Pro Cys Leu Leu Arg Arg Asn Tyr Ser Arg Glu Gln His
            20                  25                  30

Gly Val Ala Ala Ser Cys Leu Glu Asp Leu Arg Ser Lys Ala Cys Asp
        35                  40                  45

Ile Leu Ala Ile Asp Lys Ser Leu Thr Pro Val Thr Leu Val Leu Ala
    50                  55                  60

Glu Asp Gly Thr Ile Val Asp Asp Asp Tyr Phe Leu Cys Leu Pro
 65                  70                  75                  80

Ser Asn Thr Lys Phe Val Ala Leu Ala Ser Asn Glu Lys Trp Ala Tyr
                85                  90                  95

Asn Asn Ser Asp Gly Gly Thr Ala Trp Ile Ser Gln Glu Ser Phe Asp
            100                 105                 110

Val Asp Glu Thr Asp Ser Gly Ala Gly Leu Lys Trp Lys Asn Val Ala
        115                 120                 125

Arg Glu Leu Lys Glu Asp Leu Ser Ser Ile Ile Leu Leu Ser Glu Glu
    130                 135                 140

Asp Leu Gln Met Leu Val Asp Ala Pro Cys Ser Asp Leu Ala Gln Glu
145                 150                 155                 160

Leu Arg Gln Ser Cys Ala Thr Val Gln Arg Leu Gln His Thr Leu Gln
                165                 170                 175

Gln Val Leu Asp Gln Arg Glu Glu Arg Gln Ser Lys Gln Leu Leu
            180                 185                 190

Gln Leu Tyr Leu Gln Ala Leu Glu Lys Glu Gly Ser Leu Leu Ser Lys
        195                 200                 205

Gln Glu Glu Ser Lys Ala Ala Phe Gly Glu Glu Val Asp Ala Val Asp
    210                 215                 220

Thr Gly Met Ser Arg Glu Thr Ser Ser Asp Val Ala Leu Ala Ser His
225                 230                 235                 240

Ile Leu Thr Ala Leu Arg Glu Lys Gln Ala Pro Glu Leu Ser Leu Ser
                245                 250                 255

Ser Gln Asp Leu Glu Leu Val Thr Lys Glu Asp Pro Lys Ala Leu Ala
            260                 265                 270

Val Ala Leu Asn Trp Asp Ile Lys Lys Thr Glu Thr Val Gln Glu Ala
        275                 280                 285

Cys Glu Arg Glu Leu Ala Leu Arg Leu Gln Gln Thr Gln Ser Leu His
    290                 295                 300

Ser Leu Arg Ser Ile Ser Ala Ser Lys Ala Ser Pro Gly Asp Leu
305                 310                 315                 320

Gln Asn Pro Lys Arg Ala Arg Gln Asp Pro Thr
                325                 330
```

```
<210> SEQ ID NO 5
<211> LENGTH: 26
<212> TYPE: DNA
<213> ORGANISM: Artificial Sequence
<220> FEATURE:
<221> NAME/KEY: modified_base
<222> LOCATION: (6)..(12)
<223> OTHER INFORMATION: N = Inosine
<221> NAME/KEY: modified_base
<222> LOCATION: (11)..(15)
<223> OTHER INFORMATION: R = A or G
<221> NAME/KEY: modified_base
<222> LOCATION: (18)..(24)
<223> OTHER INFORMATION: Y = C or T
<221> NAME/KEY: modified_base
<222> LOCATION: (10)
<223> OTHER INFORMATION: W = A or T
<223> OTHER INFORMATION: Description of Artificial Sequence: Synthetic
      Primer

<400> SEQUENCE: 5
gaggtnganw rngartaytt ytaygg                                           26

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
atttaggtga cactatagaa                                                  20

<210> SEQ ID NO 7
<211> LENGTH: 26
<212> TYPE: DNA
<213> ORGANISM: Artificial Sequence
<220> FEATURE:
<221> NAME/KEY: modified_base
<222> LOCATION: (3)
<223> OTHER INFORMATION: R = A or G
<221> NAME/KEY: modified_base
<222> LOCATION: (6)..(24)
<223> OTHER INFORMATION: Y = C or T
<221> NAME/KEY: modified_base
<222> LOCATION: (15)..(21)
<223> OTHER INFORMATION: N = Inosine
<223> OTHER INFORMATION: Description of Artificial Sequence: Synthetic
      Primer

<400> SEQUENCE: 7
gartayttyt ayggnytnyt nttyac                                           26

<210> SEQ ID NO 8
<211> LENGTH: 17
<212> TYPE: DNA
<213> ORGANISM: Artificial Sequence
<220> FEATURE:
<221> NAME/KEY: modified_base
<222> LOCATION: (3)..(9)
<223> OTHER INFORMATION: Y = C or T
<221> NAME/KEY: modified_base
<222> LOCATION: (6)
<223> OTHER INFORMATION: N = A, C, G or T
<221> NAME/KEY: modified_base
<222> LOCATION: (12)
<223> OTHER INFORMATION: R = A or G
<221> NAME/KEY: modified_base
<222> LOCATION: (15)
<223> OTHER INFORMATION: D = G, C or A
<223> OTHER INFORMATION: Description of Artificial Sequence: Synthetic
      Primer
```

```
<400> SEQUENCE: 8
gtytgnggyt trtadat                                              17

<210> SEQ ID NO 9
<211> LENGTH: 30
<212> TYPE: DNA
<213> ORGANISM: Homo sapiens

<400> SEQUENCE: 9
tcagagaacc taaaactagt gcacattgtc                                30

<210> SEQ ID NO 10
<211> LENGTH: 30
<212> TYPE: DNA
<213> ORGANISM: Homo sapiens

<400> SEQUENCE: 10
tgccataaga aaccaccca caagctcaac                                 30

<210> SEQ ID NO 11
<211> LENGTH: 31
<212> TYPE: DNA
<213> ORGANISM: Homo sapiens

<400> SEQUENCE: 11
atccgatatc atgctccaga agcccaagag c                              31

<210> SEQ ID NO 12
<211> LENGTH: 58
<212> TYPE: DNA
<213> ORGANISM: Homo sapiens

<400> SEQUENCE: 12
atccctcgag tcacttgtcg tcgtcgtcct tgtagtcctg gcgtttccgc acaggctg  58

<210> SEQ ID NO 13
<211> LENGTH: 43
<212> TYPE: DNA
<213> ORGANISM: Homo sapiens

<400> SEQUENCE: 13
cccctctaga atagaaggag atatgctcca gaagcccaag agc                 43

<210> SEQ ID NO 14
<211> LENGTH: 52
<212> TYPE: DNA
<213> ORGANISM: Homo sapiens

<400> SEQUENCE: 14
atccctcgag tcaatgatga tgatgatgat gctggcgttt ccgcacaggc tg       52

<210> SEQ ID NO 15
<211> LENGTH: 40
<212> TYPE: DNA
<213> ORGANISM: Homo sapiens

<400> SEQUENCE: 15
atccctcgag gaaggagata tggaggtgac cggggacgcc                     40

<210> SEQ ID NO 16
<211> LENGTH: 33
<212> TYPE: DNA
```

```
<213> ORGANISM: Homo sapiens

<400> SEQUENCE: 16
agaatactcg agctatgtgg gatcctgtct ggc                                    33

<210> SEQ ID NO 17
<211> LENGTH: 30
<212> TYPE: DNA
<213> ORGANISM: Homo sapiens

<400> SEQUENCE: 17
gacatctcat atgctccaga agcccaagag                                        30

<210> SEQ ID NO 18
<211> LENGTH: 30
<212> TYPE: DNA
<213> ORGANISM: Homo sapiens

<400> SEQUENCE: 18
gtcaggcctc gagcaaagac caggacgtgg                                        30

<210> SEQ ID NO 19
<211> LENGTH: 9
<212> TYPE: PRT
<213> ORGANISM: Mus musculus

<400> SEQUENCE: 19

Glu Val Asp Trp Glu Tyr Phe Tyr Gly
 1               5

<210> SEQ ID NO 20
<211> LENGTH: 9
<212> TYPE: PRT
<213> ORGANISM: Mus musculus

<400> SEQUENCE: 20

Glu Tyr Phe Tyr Gly Leu Leu Phe Thr
 1               5

<210> SEQ ID NO 21
<211> LENGTH: 6
<212> TYPE: PRT
<213> ORGANISM: Mus musculus

<400> SEQUENCE: 21

Ile Tyr Lys Pro Gln Thr
 1               5
```